US011707505B2

(12) United States Patent
Al-Mohanna et al.

(10) Patent No.: US 11,707,505 B2
(45) Date of Patent: Jul. 25, 2023

(54) VCP AND FACTOR H AS VIRAL ENTRY INHIBITORS

(71) Applicant: KING FAISAL SPECIALIST HOSPITAL & RESEARCH CENTRE, Riyadh (SA)

(72) Inventors: Futwan Al-Mohanna, Riyadh (SA); Uday Kishore, Uxbridge (GB); Katharine Collison, Riyadh (SA); Valarmathy Murugiah, Uxbridge (GB); Soad Saleh, Riyadh (SA); Praveen Mathews Varghese, Uxbridge (GB)

(73) Assignee: KING FAISAL SPECIALIST HOSPITAL & RESEARCH CENTRE, Riyadh (SA)

( * ) Notice: Subject to any disclaimer, the term of this patent is extended or adjusted under 35 U.S.C. 154(b) by 0 days.

(21) Appl. No.: 16/684,630

(22) Filed: Nov. 15, 2019

(65) Prior Publication Data
US 2021/0145935 A1    May 20, 2021

(51) Int. Cl.
*A61K 38/17*    (2006.01)
*A61P 31/16*    (2006.01)

(52) U.S. Cl.
CPC .......... *A61K 38/1725* (2013.01); *A61P 31/16* (2018.01)

(58) Field of Classification Search
None
See application file for complete search history.

(56) References Cited

U.S. PATENT DOCUMENTS

| | | | |
|---|---|---|---|
| 2009/0104121 A1* | 4/2009 | Madasamy | A61K 49/0008 424/9.2 |
| 2010/0120665 A1* | 5/2010 | Kaleko | A61P 29/00 514/12.2 |
| 2011/0159018 A1 | 6/2011 | Stoiber | |

FOREIGN PATENT DOCUMENTS

| | | |
|---|---|---|
| WO | 1991/011461 | 8/1991 |
| WO | 2008/135237 A1 | 11/2008 |

OTHER PUBLICATIONS

Weston-Davies et al. (Abstracts / Molecular Immunology 47 (2010) 2198-2294) (Year: 2010).*
Ito et al. (Immunology. Dec. 1983; 50(4): 631-635) (Year: 1983).*
Murugaiah et al., Front. Immunol. Mar. 25, 2020;11:355 (Year: 2020).*
Abdul-Aziz, Munirah et al. "Complement factor H interferes with *Mycobacterium bovis* BCG entry into macrophages and modulates the pro-inflammatory cytokine response," Immunology, vol. 221, No. 9, pp. 944-952, Sep. 9, 2016.
Murugaiah, Valarmathy et al. "Complement-Independent Modulation of Influenza A Virus Infection by Factor H," Frontiers In Immunology, vol. 11, Mar. 25, 2020.
European Search Report issued in parallel European Application No. EP 20205760.0 dated Mar. 26, 2021.

* cited by examiner

*Primary Examiner* — Sergio Coffa
(74) *Attorney, Agent, or Firm* — Saliwanchik, Lloyd & Eisenschenk

(57) ABSTRACT

The present invention further relates to using vaccinia virus complement control protein (VCP), factor H and/or a complement control protein (CCP)-containing protein as modulator of the entry and/or replication of pathogen(s), wherein the pathogen is a virus or bacteria. The present invention further relates to a method of prevention and/or treatment of influenza A virus (IAV) infection in a subject of need thereof and to a method of modulation of the entry and/or replication of pathogen(s) in a subject of need thereof.

11 Claims, 16 Drawing Sheets

Specification includes a Sequence Listing.

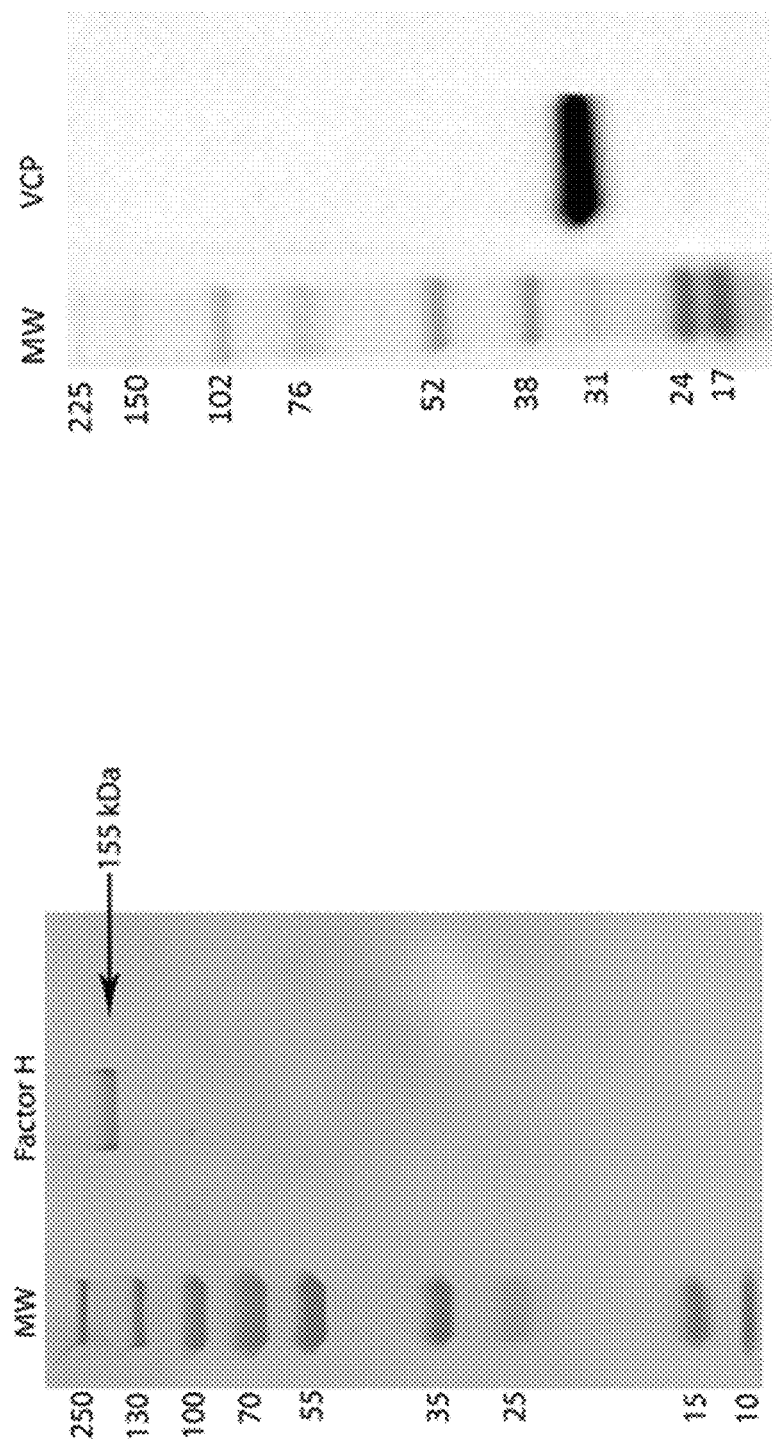

| μg/ml | IAV | | | | | 0 (PBS) |
|---|---|---|---|---|---|---|
| | 20 | 10 | 5 | 2.5 | 0 | |
| HK/99 (H3N2) | ✗ | ✗ | ✗ | ✗ | ✓ | ✗ |
| Ud/72 (H3N2) | ✗ | ✗ | ✓ | ✓ | ✓ | ✗ |
| WSN/33 (H1N1) | ✓ | ✗ | ✗ | ✗ | ✓ | ✗ |
| HK/98 (H1N1) | ✓ | ✗ | ✗ | ✓ | ✓ | ✗ |
| Eng/09 (pH1N1) | ✓ | ✗ | ✗ | ✗ | ✓ | ✗ |

FIG. 2B

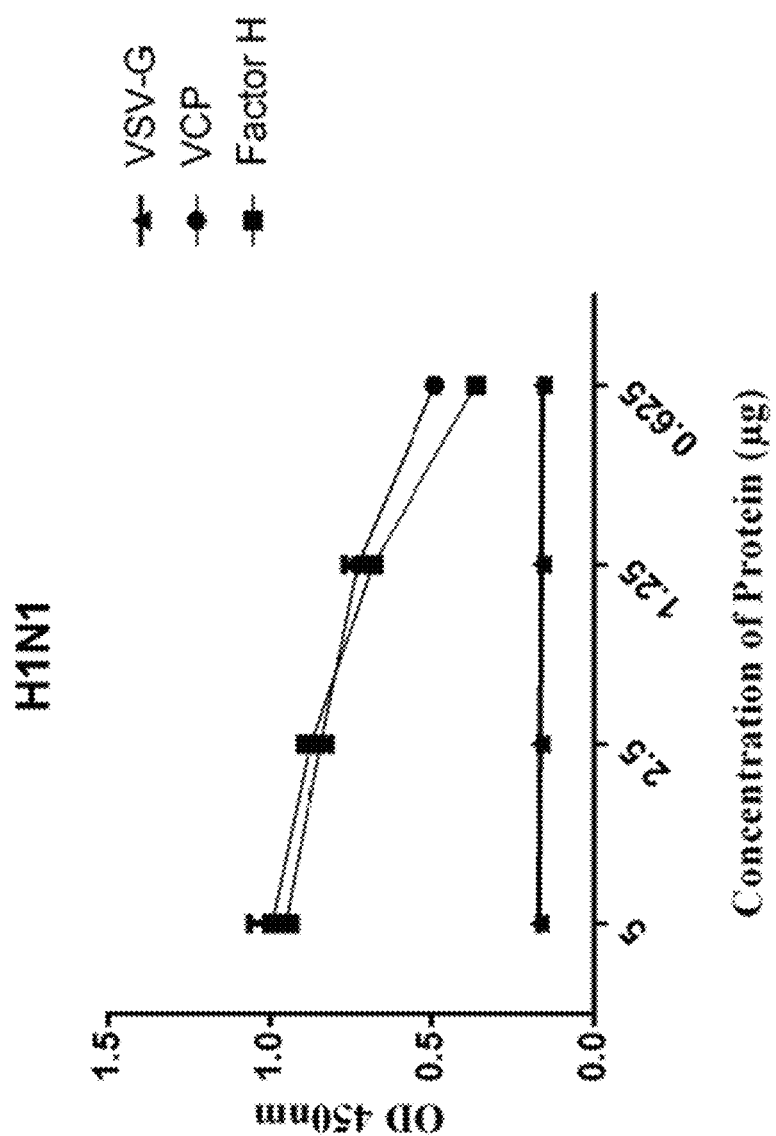

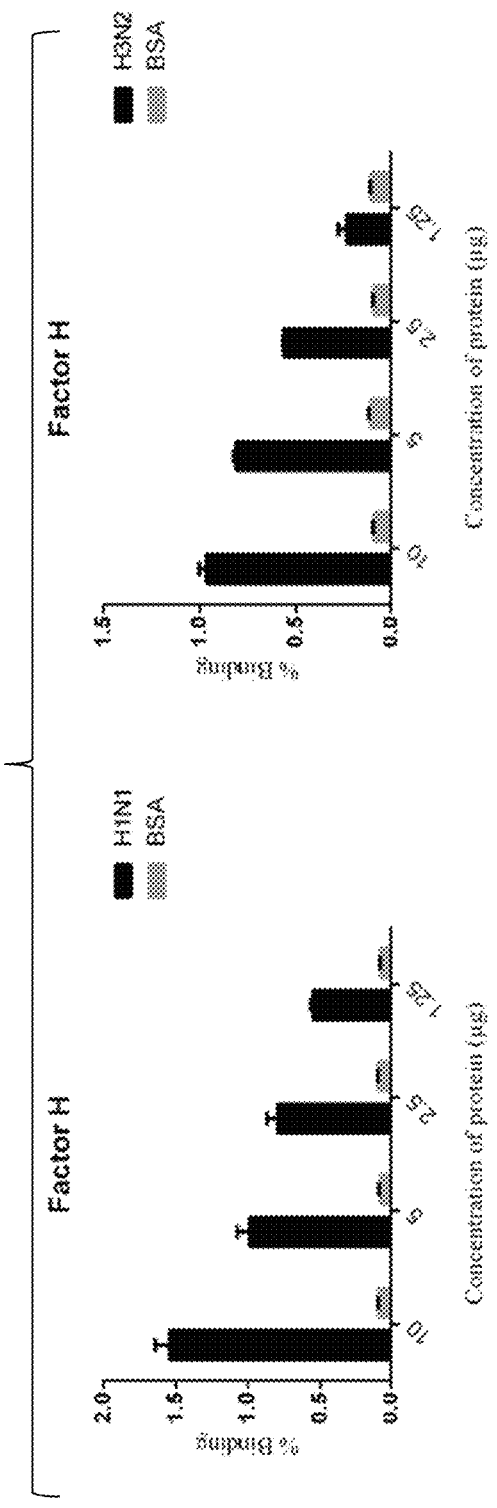
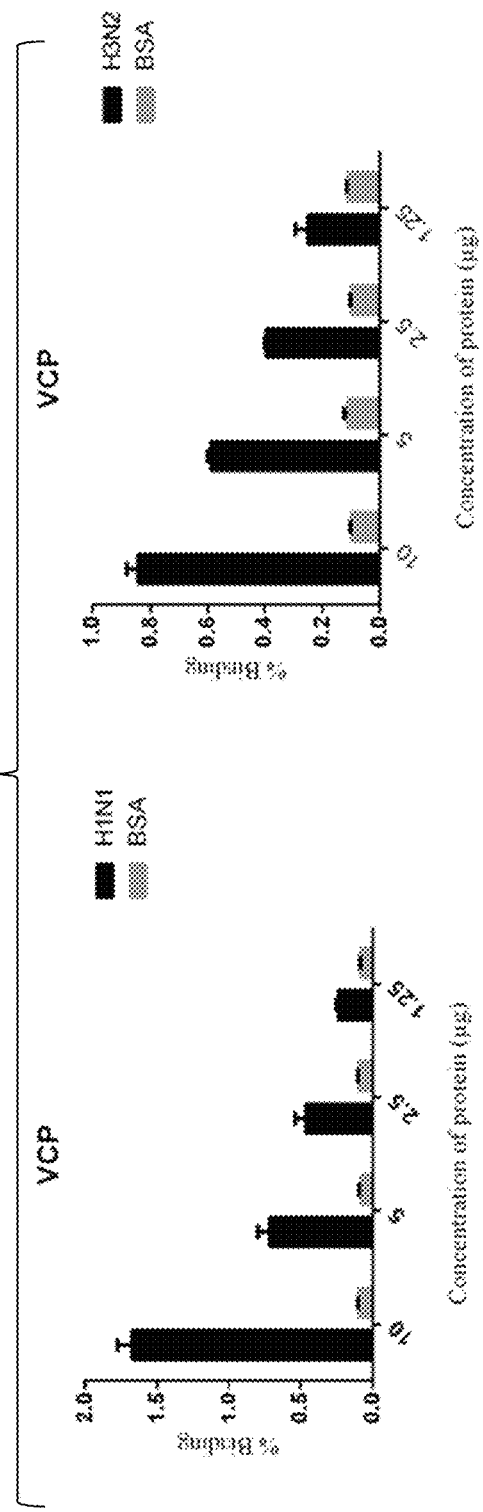
FIG. 4A
FIG. 4B

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
atggccgttc ttagttggtg                                                  20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cgctgagcca gtcagtgtag                                                  20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gaaagcagca aagaggcact                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tttcaccagg caagtctcct                                                  20
```

```
<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
aacttgcagc tgaagccatt                                           20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gacctgaacg cagaatgtca                                           20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
agcccatgtt gtagcaaacc                                           20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tgaggtacag gccctctgat                                           20

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
aaacatatgt ctgataacga aggagaacag ttctt                          35

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
gctgaattct acctcatggt cttcttga                                  28

<210> SEQ ID NO 11
<211> LENGTH: 22
<212> TYPE: DNA
<213> ORGANISM: Artificial Sequence
<220> FEATURE:
<223> OTHER INFORMATION: Primer
```

```
<400> SEQUENCE: 11
gcgggtacca tgaagatctc tg                                              22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gggtcagaat caagaaaccc tc                                              22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tttctcctgc ctgaaggaca g                                               21

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gctcatgatt tctgctctga ca                                              22
```

VCP AND FACTOR H AS VIRAL ENTRY INHIBITORS

The Sequence Listing for this application is labeled "SeqList-14Nov19-ST25.txt", which was created on Nov. 14, 2019 and is 3 KB. The entire content is incorporated herein by reference in its entirety.

FIELD OF THE INVENTION

The present invention relates to vaccinia virus complement control protein (VCP), factor H and/or a complement control protein (CCP)-containing protein for use in a method of prevention and/or treatment of influenza A virus (IAV) infection. The present invention further relates to using vaccinia virus complement control protein (VCP), factor H and/or a complement control protein (CCP)-containing protein as modulator of the entry and/or replication of pathogen(s), wherein the pathogen is a virus or bacteria. The present invention further relates to a method of prevention and/or treatment of influenza A virus (IAV) infection in a subject of need thereof and to a method of modulation of the entry and/or replication of pathogen(s) in a subject of need thereof.

BACKGROUND OF THE INVENTION

Influenza A viruses (IAVs) are severe respiratory pathogens, belonging to the Orthomyxoviridae family, representing an ongoing outbreak with high morbidity and mortality in both humans and animals (Cox et al., 2004). IAV is characterised by genetic and antigenic variations within two major surface glycoproteins, hemagglutinin (HA) and neuraminidase (NA). HA is the most significant viral glycoprotein that can bind to the host cell, causing cellular fusion and viral entry. Thus, HA-mediated epitopes are also suggested to trigger synthesis of neutralising antibodies by B cells, and greater HA variability can allow IAV to escape from immune surveillance, leading to seasonal epidemics. NA cleaves sialic acid (SA) moieties, and induces the release of virions, and promotes IAV dispersion. There are around 16 antigenic variants of HA reported, and 9 of NA, which are found in numerous combinations and subtypes (Webster et al., 1992, Fouchier et al., 2005). Among all subtypes of IAV, both H1N1 and H3N2 strains are the most predominant IAV variants in humans, and affects approximately five million individuals, causing half a million deaths in susceptible individuals (WHO, 2016). Thus, the currently circulating human IAV is likely to continuously change the antigenicity of HA and NA glycoproteins by mutation and antigenic shift (Medina et al., 2011; Tscherne et al., 2011). Therefore, such alterations aid the virus to disarm the host immune system, and promote their replication and invasion rapidly.

Airway and alveolar epithelial cells are the primary target site for IAVs, which consist of SA glycans as receptors, thus, cause damage to alveolar epithelium. Hence, individuals infected with IAVs may become susceptible to acute respiratory distress syndrome (ARDS) (Herold et al., 2015; Hogan et al., 2014). Respiratory epithelial cells express mucin glycoproteins, such as MUC5AC, MUC5B, and MUC1, which play an important role in restricting IAV infectivity (Mcauley et al., 2017). These mucins are rich in SA, serve as viral receptor, and restrict viral binding to the target cells (Mcauley et al., 2017). However, NA can inactivate the biological activity of these mucins, and attenuate their activity (Yang et al., 2016). D151G mutation is a well-known mutation in NA glycoprotein, which is responsible for its interaction with human α2-6 and avian α2-3 SA, mediating the H3N2 viral association with SA receptors. However, such mutation is reported to reduce the enzymatic action of NA that is required for HA detachment from its receptors (Yang et al., 2016). Early defense against invading IAVs by the innate immune system is crucial in limiting viral replication and invasion, thus, triggering subsequent activation of adaptive immunity. Complement system as a major humoral wing of the innate immunity offers crucial defense mechanism against IAV infection (Rattan et ah, 2013); these mechanisms include neutralisation, aggregation, opsonisation and lysis of viral particles, and induction of phagocytosis via complement receptors. In vitro and in vivo studies have demonstrated the protective role of complement system against IAVs (see e.g. Kandasamy et al., 2013).

Thus, there is a need in the art for improved means and methods for preventing and/or treating IAV infections and for modulating the entry and/or replication of viral and bacterial pathogens.

BRIEF SUMMARY OF THE INVENTION

According to the present invention this object is solved by vaccinia virus complement control protein (VCP), factor H and/or a complement control protein (CCP)-containing protein for use in a method of prevention and/or treatment of influenza A virus (IAV) infection.

According to the present invention this object is solved by using vaccinia virus complement control protein (VCP), factor H and/or a complement control protein (CCP)-containing protein as modulator of the entry and/or replication of pathogen(s), wherein the pathogen is a virus or bacteria According to the present invention this object is solved by a method of prevention and/or treatment of influenza A virus (IAV) infection in a subject of need thereof, comprising the administration of a therapeutically amount of VCP, factor H and/or CCP-containing protein, or a domain of VCP, factor H and/or CCP-containing protein, wherein said domain is a complement regulatory domain, preferably a contiguous complement control protein (CCP) domain According to the present invention this object is solved by a method of modulation of the entry and/or replication of pathogen(s) in a subject of need thereof, comprising the administration of a therapeutically amount of VCP, factor H and/or contiguous complement control protein (CCP)-containing protein, or a domain of VCP, factor H and/or CCP-containing protein, wherein said domain is a complement regulatory domain, preferably a CCP domain, more preferably CCP18-20 of factor H, wherein the pathogen is a virus or bacteria.

The following examples and drawings illustrate the present invention without, however, limiting the same thereto.

BRIEF DESCRIPTION OF THE DRAWINGS

FIGS. 1A-1C. 12% (w/v) SDS-PAGE analysis of purified complement factor H using human Plasma (1A) and a recombinant form of vaccinia virus complement control protein (VCP) from HEK-293 cells transfected with VCP gene (1B). The sample was ran under reducing condition, and purified factor H appeared as ~155 kDa band, and VCP was evident at ~35 kDa. Secreted a recombinant from of VCP by HEK-293 cells was purified through heparin column, and eluted with a linear salt gradient (0 to 0.5 M NaCl). Fractions were collected and analysed via gel filtration, and Peak 3 is VCP (1C).

FIGS. 2A-2B. Inhibition of hemagglutination by purified human factor H was tested on human IAV subtypes. Guinea pig red blood cells were either incubated with PBS or IAV subtypes with and without varied concentration of purified factor H (20, 10, 5, and 2.5 µg). ✓—hemagglutination occurred; X—no hemmaglutination or inhibition of hemagglutination. PBS control—no virus was added.

FIGS. 3A-3B. The binding interaction between factor H, VCP with pH1N1 (3A), and H3N2 (3B) IAV subtypes were determined via ELISA. Microtiter wells were coated with varied concentrations of purified CFH, VCP and VSV-G (5, 2.5, 1.25, and 0.625 µg/well) in the presence of carbonate bicarbonate buffer overnight under cold condition. 50 μl of concentrated pH1N1 or H3N2 virus (1.36x106 pfu/ml) was added to each well in the presence of 5 mM $CaCl_2$, and probed with either monoclonal anti-influenza virus H1 or polyclonal anti-influenza virus H3 antibody. VSV-G pseudotyped particle was used as a negative RNA virus control. The data were expressed as mean of three independent experiments done in triplicates±SEM.

FIGS. 4A-4B. Cell-binding assay to show binding of factor H (4A) and VCP (4B) to A549 cells challenged with H1N1 and H3N2. A549 cells ($1\times10^5$ cells/ml) were seeded in a 96 microtiter wells, and incubated at 37° C. overnight. A varied concentration of factor H and VCP (10, 5, 2.5, and 1.25 μg), pre-incubated IAV subtypes were added to the corresponding wells, and incubated at room temperature for 1 h. After removing excess protein and viral particles, the wells were fixed with 4% paraformaldehyde. The corresponding wells were probed with monoclonal anti-influenza virus H1, or polyclonal anti-influenza virus H3 antibodies. Maltose-binding protein (MBP) was used as a negative control protein, and weaker binding was observed. Three independent experiments were carried out in triplicates and error bars expressed as ±SEM.

FIGS. 5A-5E. Far western blot analysis to show factor H (5A) and VCP (5B) binding interaction with purified pH1N1 and H3N2. 20 μl of concentrated IAV subtypes ($1.36\times10^6$ pfu/ml) were first run on the SDS-PAGE under reducing conditions, and transferred onto a nitrocellulose membrane. The transferred membrane was then incubated with 10 μg/ml of factor H and VCP. The membrane was probed with either monoclonal mouse anti-human factor H, or polyclonal rabbit anti-VCP antibody. Factor H and VCP bound to HA (~70 kDa), NA (~55 kDa) and M1 (~25 kDa) in the case of both IAV subtypes. The identity of factor H and VCP bound IAV glycoproteins was validated using a separate blot that was directly probed with monoclonal anti-HA (5C), anti-NA (5D), and anti-M1 (5E) antibodies.

FIGS. 6A-6B. Replication of IAV subtypes (pH1N1 and H3N2) Is restricted by factor H (6A) and VCP (6B) in target human A549 cells. M1 expression of both pH1N1 and H3N2 IAV subtypes (MOI 1) after infection of A549 cells at 6 h. A549 cells were incubated either with pre-incubated pH1N1 and H3N2 with purified factor H and VCP (40 μg/ml) or without purified factor H or VCP. Cell pellets were harvested at 6 h to analyze the M1 expression of IAV. The RNA extracted from lysed cell pellet was converted into cDNA. Infection was measured via qRT-PCR using M1 primers and 18S was used as an endogenous control. Significance was determined using the unpaired one-way ANOVA test (***p<0.001, and 0.0001) (n=3).

FIGS. 7A-7B. Transcription expression profile of cytokines and chemokines produced by A549 in response to H1N1 (7A) and H3N2 (7B) challenge with and without factor H (40 μg/ml). mRNA expression levels of cytokines and chemokines were measured using qRT-PCR and the data were normalized using 18S expression as an endogenous control. Cells only was used as a calibrator to calculate relative expression (RQ); RQ=2-ΔΔCt. Experiments were conducted in triplicates, and error bars represents ±SEM. Unpaired one-way ANOVA test was used calculate the significance (*p<0.05, p<0.01, *p<0.001, and ****p<0.0001) (n=3). The RQ value was calculated using the formula.

FIGS. 8A-8C. mRNA expression profile of cytokines/chemokines secreted by H1N1 (8A) and H3N2 (8B) infected A549 cells, pre-treated with VCP (40 μg/ml). Expression levels of type I interferon alpha (IFN-α) following 6 h treatments with factor H and VCP (8C). mRNA expression was normalized via 18S endogenous control. RQ=2-ΔΔCt was used to calculate the RQ value. Significance was determined using the unpaired one-way ANOVA test (p<0.01, *p<0.001, and ****p<0.0001) (n=3). UT (untreated sample), and T (treated sample).

FIGS. 9A-9B. Western blotting to show expression of hemagglutinin (HA) in purified H1N1 and H3N2 pseudotyped lentiviral particles (9A). HA expression was evident at ~70 kDa. Luciferase reporter activity of H1N1 and H3N2 lentiviral transduced cells with and without factor H and VCP (9B). Significance was determined using the unpaired one-way ANOVA test (*p<0.05 and ***p<0.001) (n=3).

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "0.1 to 20" should be interpreted to include not only the explicitly recited values of 0.1 to 20, but also include individual values and sub-ranges within the indicated range. Thus, included in this numerical range are individual values such as 0.1, 0.2, 0.3, 0.4, 0.5, 0.6, 0.7, 0.8, 0.9, 1, 1.1 . . . 19.6, 19.7, 19.8, 19.9, 20 and sub-ranges such as from 1 to 10, 0.5 to 5, etc. This same principle applies to ranges reciting only one numerical value, such as "at least 90%". Furthermore, such an interpretation should apply regardless of the breadth of the range or the characteristics being described.

VCP, Factor H or CMP-Containing Proteins for Preventing and/or Treating IAV Infections As discussed above, the present invention provides
vaccinia virus complement control protein (VCP),
factor H and/or
a complement control protein (CCP)-containing protein
for use in a method of prevention and/or treatment of influenza A virus (IAV) infection.

Factor H

Figure 1C:
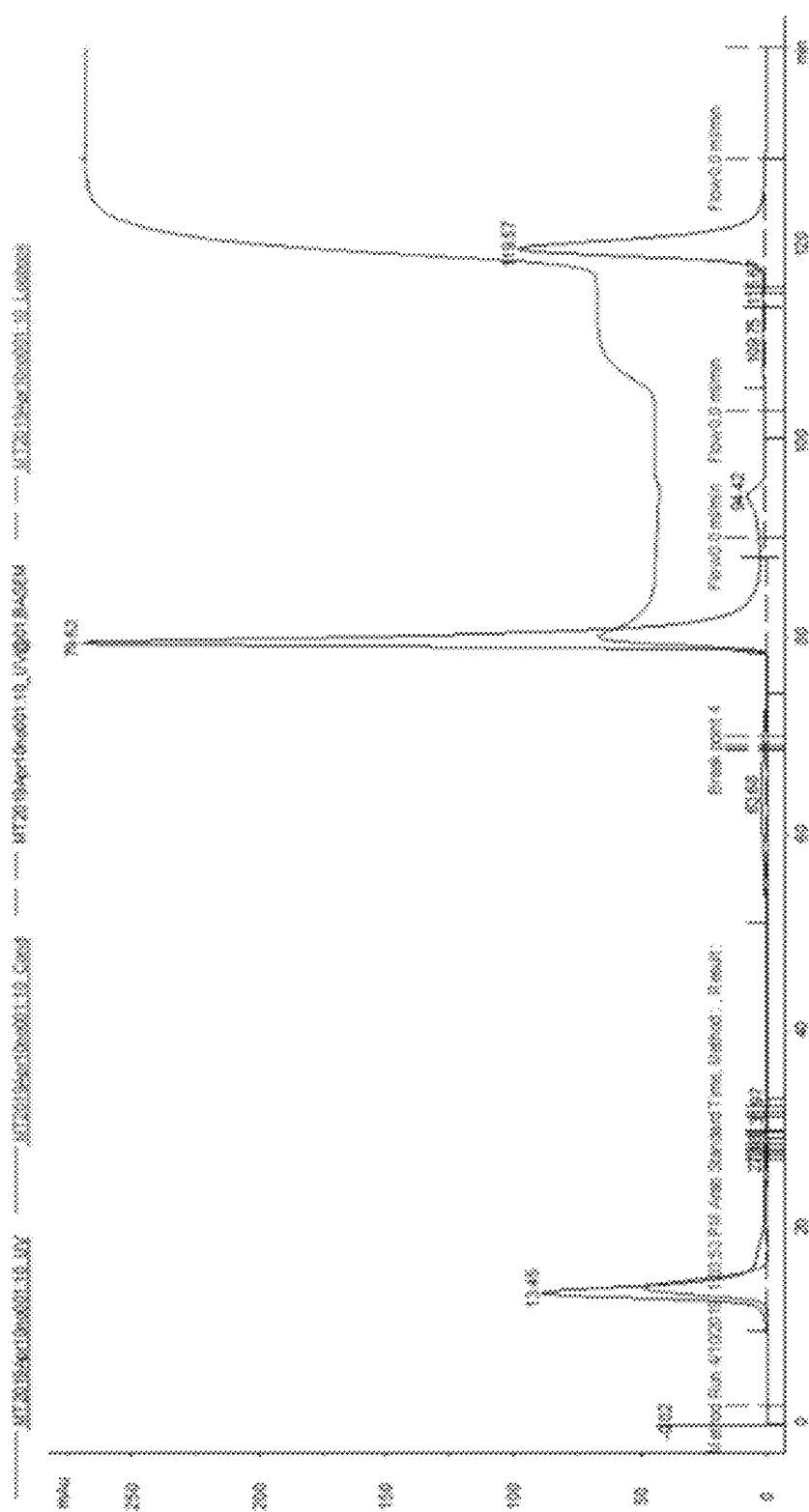

Certain complement regulators including Factor H and properdin, have been shown to bind to IAV. In the alternative pathway, Factor H is an important negative regulator that interacts with negatively charged membranes containing sialic acids and glycosaminoglycan, and protects cellular structures from C3 convertase formation, hence complement activation.

Factor H is a soluble 155 kDa plasma glycoprotein at a concentration of 128-654 µg/ml in human plasma (Ansari et al., 2013). It is composed of 20 complement control protein (CCP) modules with different binding properties. There is plenty of evidence of the local synthesis of factor H extra-hepatically. Factor H has acquired the ability to bind a number of pathogens via charge interactions (Lambris et al., 2008), and for pathogens, surface-bound factor H may benefit their survival.

Factor H has a regulatory function in the homeostasis of the complement system and in the protection of bystander host cells and tissues from injury via complement activation. The most significant point in the complement activation is the regulation of C3 convertase, which is monitored by factor H, a well-established sialic acid binder. A number of bacteria can acquire factor H via the presentation and interaction of specific binding partner proteins; including factor H binding proteins (fHbp) of *Neisseria meningitides* (Pizza et al., 2008), CspA and the outer surface protein E of *Borrelia burgdorferi* (Kraiczy et al., 2004; Hellwage et al., 2001), the staphylococcal binder of IgG from *Staphylococcus aureus* (Haupt et al., 2008), and the pneumococcal surface protein C of *Streptococcus pneumoniae* (Janulczyk et al., 2000). Furthermore, *Plasmodium falciparum* has also shown to bind factor H and factor H-like protein-1 (FHL-1) to prevent complement mediated lysis in the mosquito midgut (Simon et al. 2013) via the plasmodial transmembrane gliding-associated protein 50 (GAP50). Moreover, plasma purified human factor H can bind the surface of *mycobacterium*, and restrict the uptake of *M. bovis* BCG by macrophages, and modulates inflammatory cytokine responses (Abdul-Aziz el al. 2016).

The factor H ligands, expressed by these organisms, are structurally distinct from each other, but they are suggested to share the related binding site on factor H that is shown to be localized on a common site of CCP20 module (Meri et al., 2013). These interactions increase the binding ability of CCP19-20 modules to C3b, resulting in a stable complex between factor H, C3b and microbial proteins, with an enhanced co-factor activity.

Vaccinia Virus Complement Control Protein (TCP)

Several studies have demonstrated that viruses use diverse mechanisms to protect their viral lipid envelopes from complement lysis by encoding or recruiting complement inhibitors (factor I and factor H), with structural and functional similarities to complement control proteins.

Vaccinia virus complement control protein (VCP) is a well-known complement inhibitor, secreted by vaccinia virus infected cells. VCP has inhibitory activity of both classical and alternative trigger of complement cascade (Kotwal et al. 1990). Examples includes binding of West Nile virus non-structural protein (NS1) to factor H, or incorporation of Nipah virions with factor I, thus, restriction of complement activation. In addition, NS1 serve as a key inhibitor innate immunity as it is shown to block the synthesis and signalling of type 1 interferons (IFNs) (Qian et al. 2017). NS1 is also reported to induce apoptosis in human airway epithelial cells during IAV infection via caspase-dependent mechanisms (Lam et al. 2008).

VCP is a 35 kDa secretory protein, encoded by the C3L open reading frame (ORF). VCP contains four short consensus repeats (Kotwal et al. 1990). Studies have validated the ability of VCP to protect the infected cells, and released viral particles from the complement attack of the host cell (Isaacs et al. 1992).

Complement Control Protein (NCR)-Containing Proteins

The complement system distinguishes "self" from "non-self" via a range of specialized cell-surface and soluble proteins. These homologous proteins belong to a family called the "regulators of complement activation (RCA)" or "complement control proteins (CCP)". Complement control proteins work in concert to regulate the complement system and keep it from damaging host tissue while simultaneously directing it towards foreign particles such as viruses and bacteria, and unwanted material such as cell debris and antibody-antigen complexes. Most of the complement control proteins act on the convertases, C3b and C4b, which are bimolecular complexes formed early on in the complement cascade.

In one embodiment, the CPP-containing protein is a C4b binding protein.

Domains

In a preferred embodiment, a domain of VCP, factor H and/or a CCP-containing protein is used.

Said domain is a complement regulatory domain, preferably a CCP domain. In a preferred embodiment, the CCP domain is CCP18-20 of factor H.

Preferably, the prevention and/or treatment of influenza A virus (IAV) infection comprises modulation of IAV infectivity, wherein said modulation of IAV infectivity is preferably dependent on the IAV strain.

Preferably, the modulation of the inflammatory response in IAV infection is comprised.

In one embodiment, the VCP, factor H, CCP-containing protein and/or a respective domain of VCP, factor H or CCP-containing protein is administered intranasal, intratracheal and/or sublingual.

Uses of VCP, Factor H or CCP-Containing Proteins as Modulator (s) of the Entry and/or Replication of Pathogen(s)

As discussed above, the present invention provides the use of
vaccinia virus complement control protein (VCP),
factor PI, and/or
a complement control protein (CCP)-containing protein
as modulator(s) of the entry and/or replication of pathogen (s).

According to the invention, the pathogen is a virus or bacteria.

For example, the CPP-containing protein is a C4b binding protein.

Preferably, a domain of VCP, factor H and/or a CCP-containing protein is used, wherein said domain is a complement regulatory domain, preferably a CCP domain.

In a preferred embodiment, the CCP domain is CCP18-20 of factor H.

Preferably, the virus is influenza A vims (IAV), human immunodeficiency virus 1 (HIV-1), Respiratory Syncytial Virus (RSV), and/or Coronavirus causing Middle-East Respiratory Syndrome (MERS-CoV).

Preferably, the bacterium is *Mycobacterium tuberculosis*.

Preferably, the entry and/or replication of IAV is modulated in a strain-specific manner, such as inhibition of strain H1N1 and H3N2.

Methods or Treatment

As discussed above, the present invention provides a method of prevention and/or treatment of influenza A virus (IAV) infection in a subject of need thereof.

Said method comprises the administration of a therapeutically amount of

VCP, factor H and/or contiguous complement control protein (CCP)-containing protein, or a domain of VCP, factor H and/or CCP-containing protein, wherein said domain is a complement regulatory domain, preferably a contiguous complement control protein (CCP) domain.

In a preferred embodiment, the CCP domain is CCP18-20 of factor H.

For example, the CPP-containing protein is a C4b binding protein.

In one embodiment, the administration is intranasal, intratracheal and/or sublingual.

A "therapeutically effective amount" of VCP, factor H and/or CCP-containing protein and/or a domain thereof preferably refers to the amount necessary to achieve the therapeutic outcome. The choice of the optimal dosage regime and duration of medication, particularly the optimal dose and manner of administration of the active compounds necessary in each case can be determined by a person skilled in the art on the basis of his/her expert knowledge.

As discussed above, the present invention provides a method of modulation of the entry and/or replication of pathogen(s) in a subject of need thereof.

Said method comprises the administration of a therapeutically amount of

VCP, factor H and/or contiguous complement control protein (CCP)-containing protein, or a domain of VCP, factor H and/or CCP-containing protein, wherein said domain is a complement regulatory domain, preferably a CCP domain, more preferably CCP18-20 of factor H, According to the invention, the pathogen is a virus or bacteria.

Preferably, the virus is influenza A virus (IAV), human immunodeficiency virus 1 (HIV-1), Respiratory Syncytial Virus (RSV), and/or Coronavirus causing Middle-East Respiratory Syndrome (MERS-CoV).

Preferably, the bacterium is *Mycobacterium tuberculosis*.

For example, the CPP-containing protein is a C4b binding protein.

In a preferred embodiment, the CCP domain is CCP18-20 of factor H.

In one embodiment, the administration is intranasal, intratracheal and/or sublingual.

A "therapeutically effective amount" of VCP, factor H and/or CCP-containing protein and/or a domain thereof preferably refers to the amount necessary to achieve the therapeutic outcome. The choice of the optimal dosage regime and duration of medication, particularly the optimal dose and manner of administration of the active compounds necessary in each case can be determined by a person skilled in the art on the basis of his/her expert knowledge.

Further Description of Preferred Embodiments

Abstract

Complement system is the most ancient innate immune defense mechanism that can recognise molecular patterns on the surface of invading pathogens and triggering its activation. Factor H (fH) is an inhibitor of the alternative pathway, and down-regulates complement activation on the host cell surface. fH is locally synthesised at the site of infection and injury including lungs, and can also act as a pattern recognition molecule independent of its involvement in complement activation.

Here, we report that Factor H, a sialic acid binder interacts with influenza A virus (IAV). fH can modulate the IAV replication in a strain-dependent manner, as observed by an upregulation of M1 expression in H3N2 infected A549 cells, while downregulating M1 in H1N1 subtype. In a far western blot, fH bound hemagglutinin (~70 kDa), neuraminidase (NA), (~60 kDa), and matrix protein 1 (M1) (~25 kDa) in a calcium-dependent manner. Furthermore, transcriptional levels of IFN-α, TNF-α, IL-12, IL-6, IFN-α and RANTES were reduced following factor H treatment for H1N1 subtype at 6 h post infection in A549 lung epithelial cells. For H3N2 subtype, mRNA levels of these pro-inflammatory cytokines were enhanced, suggesting that the modulatory effect of fH is IAV subtype specific. Use of a recombinant form of vaccinia virus complement control protein (VCP), which contains CCP modules like human Factor H, mirrored the results obtained by Factor H. Additionally, both factor H (25%) and VCP (45%) were found to reduce luciferase reporter activity of MDCK cells transduced with H1N1 lentiviral pseudotypes particles. However, an opposite effect was seen in the case of cells transduced with H3N2 pseudotyped particles. fH (50%) and VCP (30%) enhanced the luciferase reporter activity, suggesting an entry inhibitory role of fH and VCP against H1N1, but not H3N2.

Our results show that innate immune complement regulators such as fH modulate IAV infection and associated inflammatory response independent of their complement regulating functions.

Discussion

Factor H is an abundant protein, which has a regulatory function in the homeostasis of the complement system and in the protection of bystander host cells and tissues from injury via complement activation. The activation of complement can take place via three pathways, such as classical, alternative and lectin. The most significant point in the complement activation is the regulation of C3 convertase, which is monitored by factor H, a well-established sialic acid binder. A number of bacteria can acquire factor H via the presentation and interaction of specific binding partner proteins; including factor H binding proteins (fHbp) of *Neisseria meningitides* (Pizza et al. 2008), CspA and the outer surface protein E of *Borrelia burgdorferi* (Kraiczy et al. 2004; Hellwage el al. 2001), the staphylococcal binder of IgG from *Staphylococcus aureus* (Haupt et al. 2008), and the pneumococcal surface protein C of *Streptococcus pneumoniae* (Janulczyk et al. 2000).

The factor H ligands, expressed by these organisms, are structurally distinct from each other, but they are suggested to share the related binding site on factor H that is shown to be localised on a common site of CCP20 module (Meri et al. 2013). These interactions increase the binding ability of CCP19-20 modules to C3b, resulting in a stable complex between factor H, C3b and microbial proteins, with an enhanced co-factor activity. Infection with *Pseudomonas aeruginosa* has become real concern with immunocompromised patients. Studies have reported that *Pseudomonas aeruginosa* express sialic acid on their surfaces, which reduce complement deposition, and siglec mediated host-cell recognition, thus, complement mediated immune response escape (Khatua et al. 2010). Factor H binds to ApoE on HDL via CCP5-7 modules, and is used by the bacteria to mimic the plasma HDL to increase their survival in the blood (Haapasalo et al. 2015).

Additionally, fungi also use similar evasion strategies to overcome innate immune response, it has been shown that *Aspergillus fumigatus* fungus recruit factor H and C4BP complement inhibitors on its cell wall (Vogl el al. 2008), but the microbial ligands are poorly studied (Heinekamp et al. 2015).

The aim of the study was to investigate the complement independent functions of factor H in the regulation of IAV infection. In addition, VCP is also reported to be an effective complement inhibitor protein, which contains CCP modules like factor H, and have complement regulatory activity (Kotwal et al. 1990). VCP is a 35 kDa secretory protein of vaccinia virus, encoded by the C3L open reading frame (ORF), and contains four short consensus repeats (Kotwal et al. 1990). Studies have validated the ability of VCP to protect the infected cells, and released viral particles from the complement attack of the host cell (Isaacs et al. 1992).

Figure 2A:
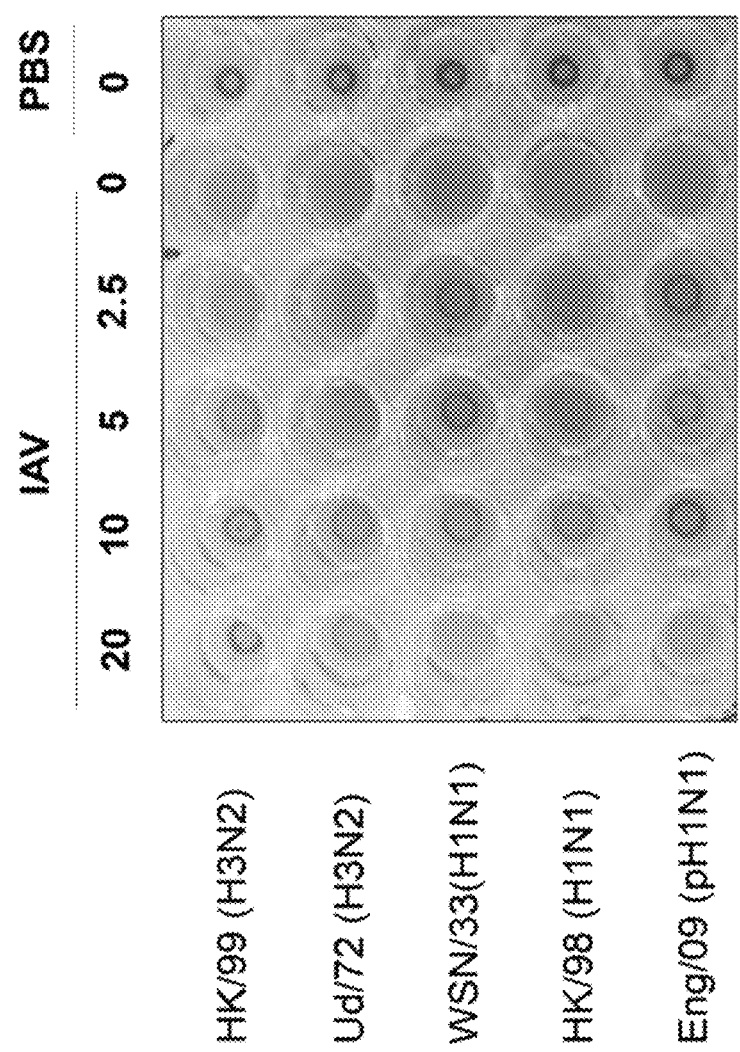
Figure 3B:
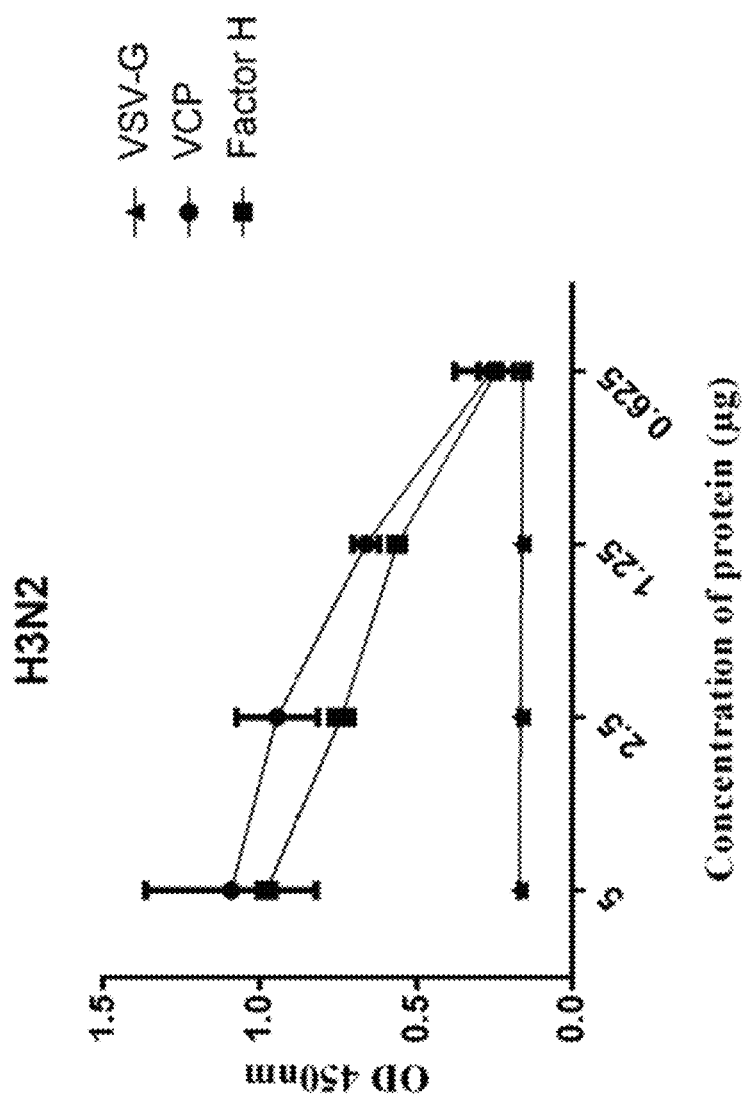
Figure 5B:
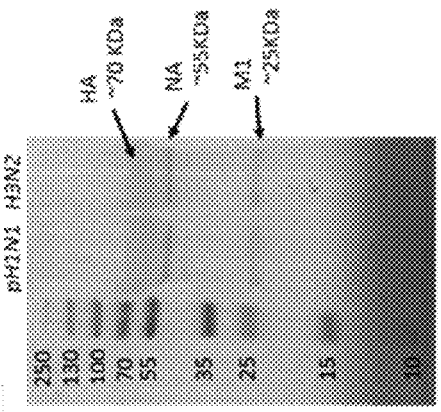
Figure 5A:
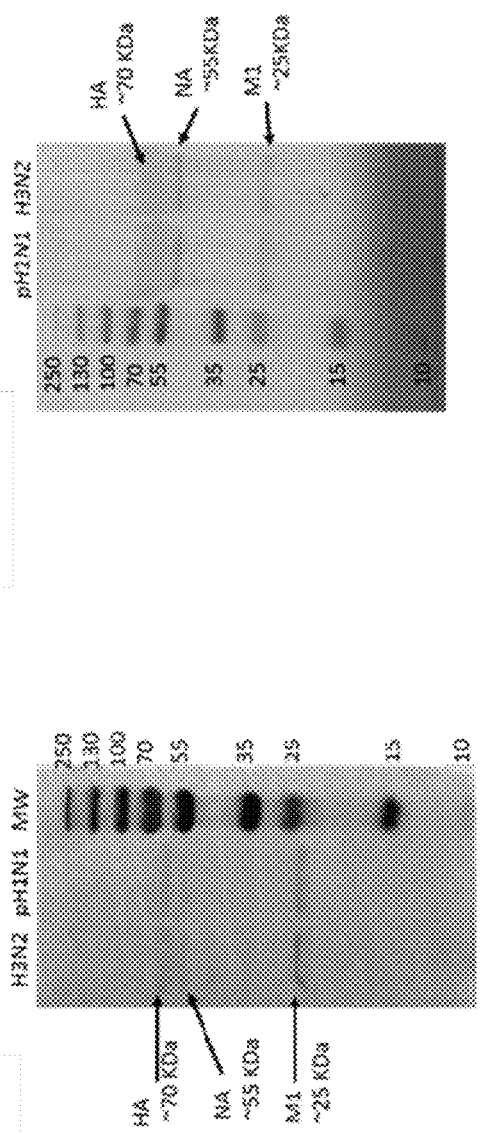
Figure 5E:
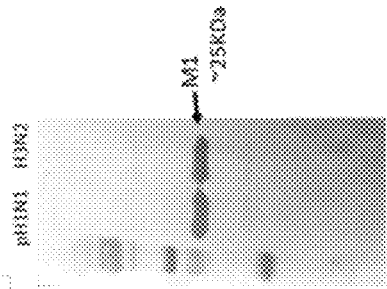
Figure 5D:
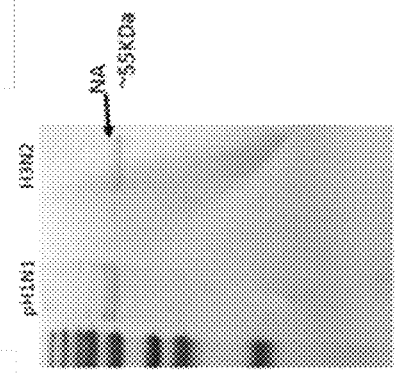
Figure 5C:
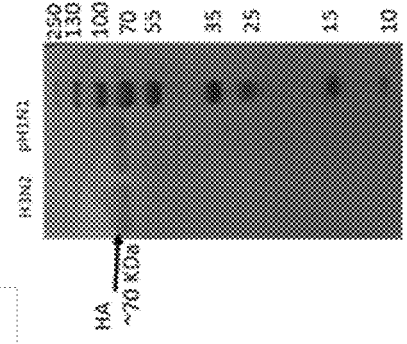

In this study, a direct and complement independent interaction of factor H and VCP with H1N1 and H3N2 IAV subtypes was examined via hemagglutination assay, ELISA, cell binding and far western blotting. Our hemagglutination assay demonstrates the ability of factor H to inhibit hemagglutination of both H1N1 and H3N2 IAV subtypes. Among varied concentration of factor H, 10 µg/ml seemed to be most effective against the H1N1 compared to H3N2 subtype (FIG. 2). VCP contain heparin binding site similar to factor H (Ganesh et al., 2004), it is possible that similar to factor H (Sahu et al. 1993; Meri et al 1990), the heparin binding site found within the VCP protein enhances its decay-accelerating action against C3 convertase; which is present on the sheep erythrocytes, which is suggested to have a high surface density of sialic acid. However, other studies suggest that the decay activity rate of VCP does not reduce on neuraminidase-treated sheep erythrocytes (Sahu et al. 1993; Meri et al 1990). Furthermore, a weaker decay rate was seen with CCP2-4 mutants of VCP, suggesting the importance of CCPs 2 to 4. The maximum binding of factor H and VCP to both H1N1 and H3N2 strains was seen at 5 µg/ml via ELISA in a calcium dependent manner (FIG. 3). Factor H seems more favourable for binding to H1N1 and H3N2 strain via HA (~70 kDa) and NA (~55 kDa) in addition to recognizing M1 (~25 kDa) as evident in far western blotting (FIG. 5). VCP mirrored the data obtained by factor H, recognising HA, NA and M1. It is well known that the viral HA can bind to sialic acid residues on surface glycoprotein and its receptor binding depends on the nature of the glycosidic linkage. The binding of HA to sialic acid compounds, like factor H is the initial event in the virus association with human epithelial cells. In addition, the resulting disruption of the neuraminic acid residues can enable the virus to cross over the epithelial cells, thus entering new cells to initiate viral replication.

Figure 6A:
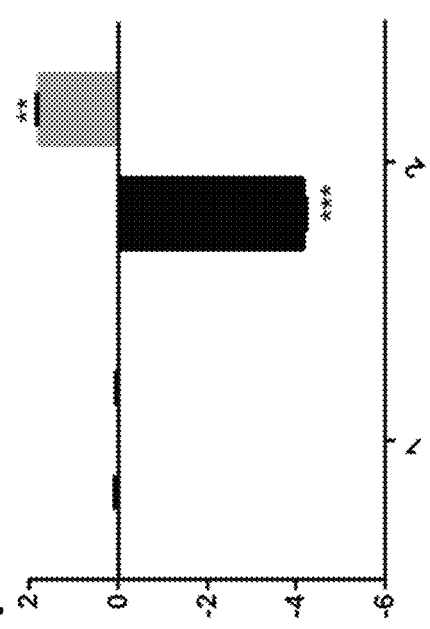
Figure 6B:
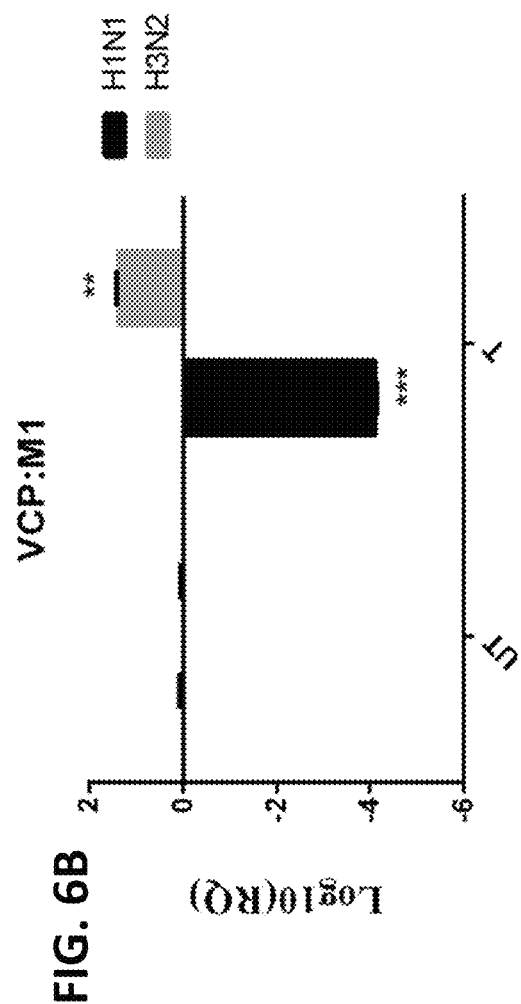

Immune response of A549 cells following IAV challenge with and without factor H and VCP was examined via infection assay and qRT-PCR. The ability of factor H and VCP to modulate viral replication was determined using M1 expression levels among protein treated and un-treated A549 cells infected with either H1N1 or PI3N2 subtype of IAV (FIG. 6). Both factor H and VCP modulated the IAV replication in a strain dependent manner as seen by an upregulation of M1 mRNA levels in H3N2 infected A549 cells, while M1 downregulation in H1N1 subtype. In the case of H1N1, both factor H and VCP showed reduced viral M1 expression ($-4\ \log_{10}$) at 6 h treatment (FIG. 6B). However, an increased M1 expression was seen with H3N2 ($2\ \log_{10}$) following factor H and VCP treatment, suggesting that the inhibitory effect of these proteins is strain-dependent. This shows that both factor H and VCP could act as an entry inhibitor against H1N1 subtype only.

Respiratory secretions of experimentally infected species have revealed altered expressions of cytokines and chemokines levels. Cytokines can either act as pro- or anti-inflammatory in the host response. Several studies have demonstrated both direct and indirect correlation between cytokine levels and viral replication. In this present study, alterations of cytokines levels were observed in H1N1 and H3N2 infected A546 cells challenged by factor H and VCP.

Figure 7A:
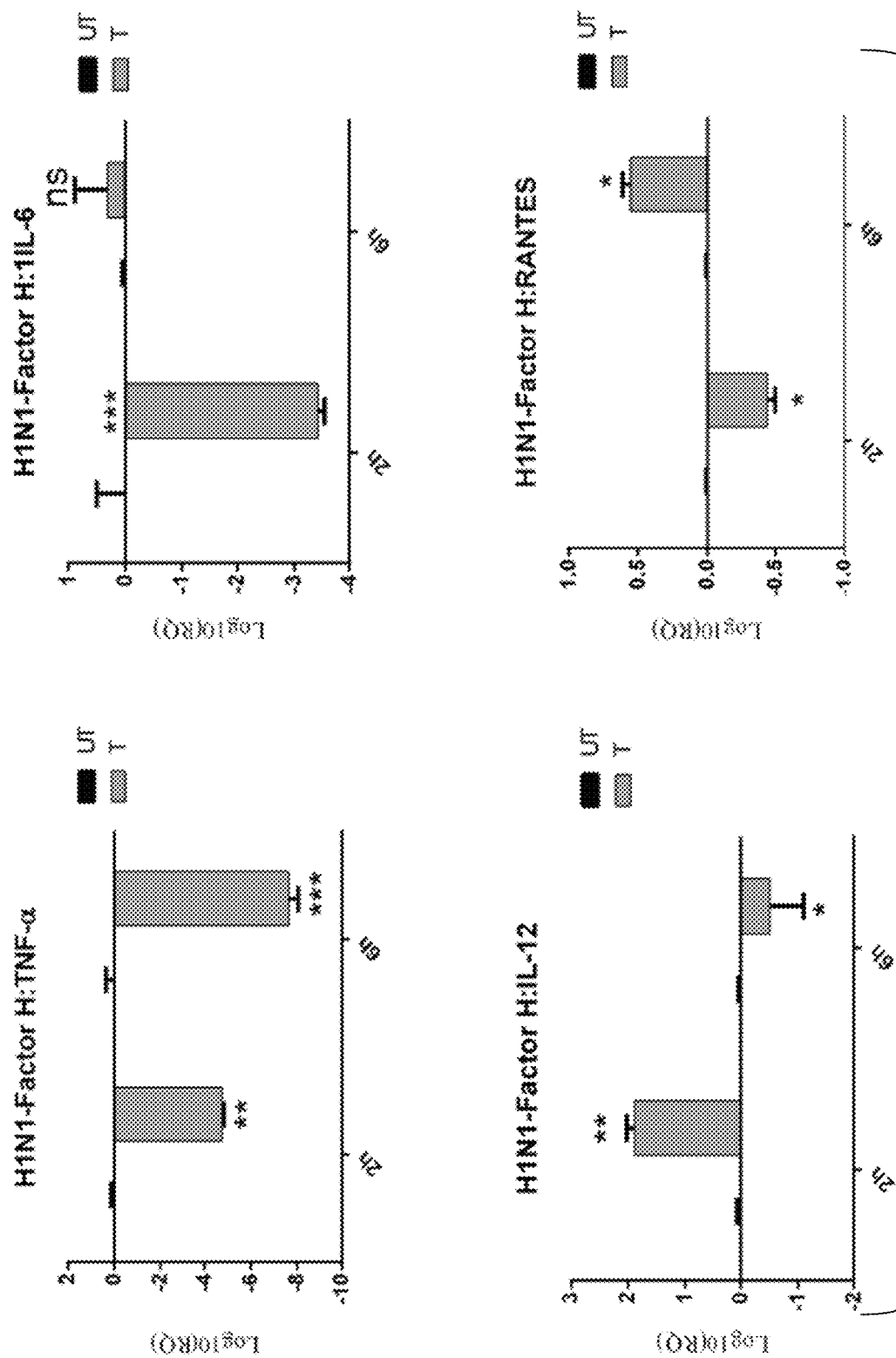
Figure 7B:
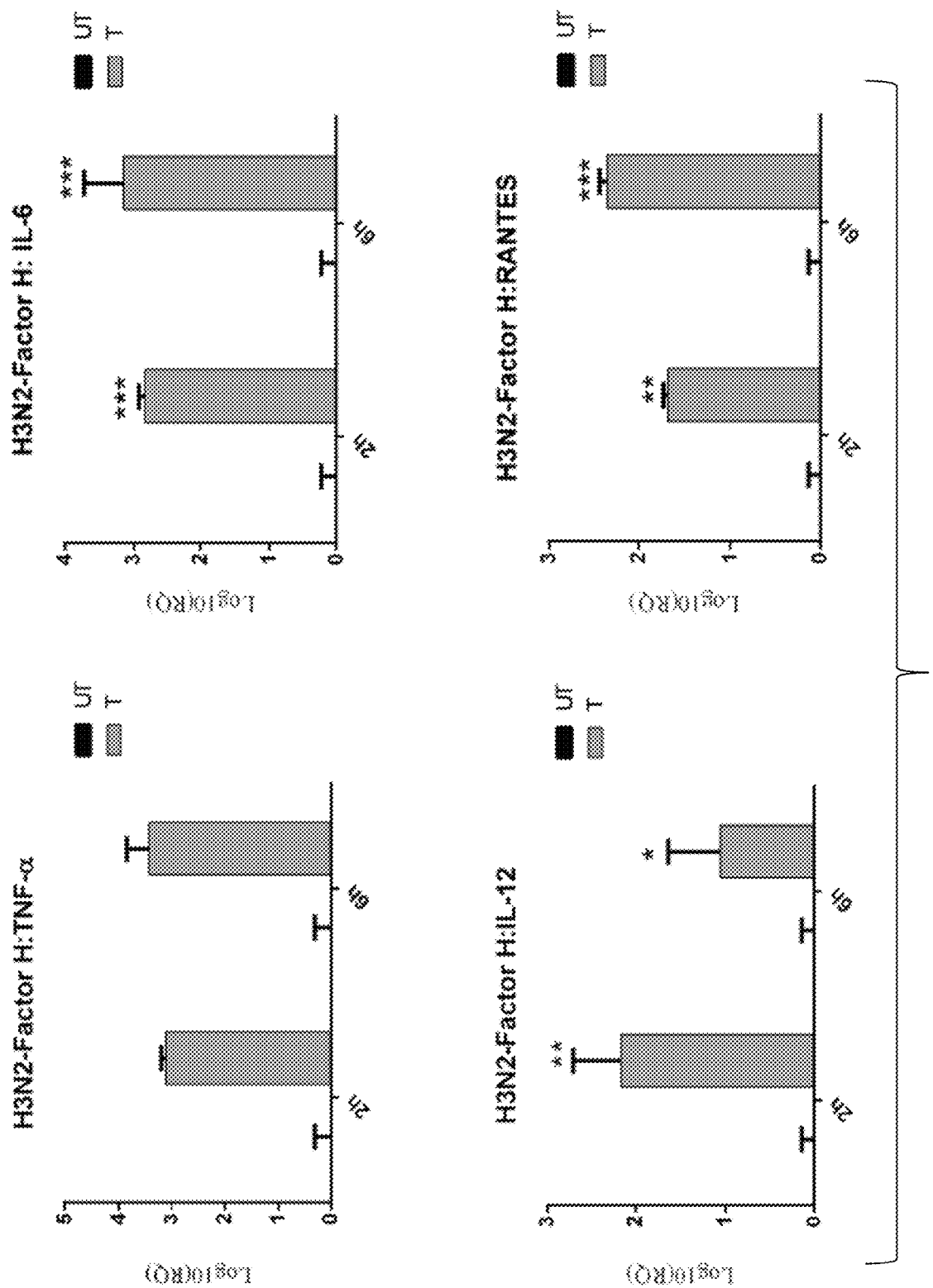

Factor H treatment resulted in downregulation of TNF-α at 2 h ($-5\ \log_{10}$) and 6 h ($-8\ \log_{10}$) in H1N1 infected cells. In the case of H3N2 infected cells, an expression level of TNF-α was up-regulated at 2 h ($3\ \log_{10}$) as well as at 6 h ($3.5\ \log_{10}$) treatment (FIGS. 7A and 7B). Reduced mRNA levels of IL-6 ($-3.5\ \log_{10}$) and RANTES ($-0.5\ \log_{10}$) were seen at 2 h treatment with Factor H, which were brought up slightly at 6 h treatment. Conversely, enhanced levels of IL-6 ($2.5\ \log_{10}$) and RANTES ($1.5\ \log_{10}$) were observed in H3N2 infected cells following 2 h and 6 h (IL-6/$3\ \log_{10}$) (RANTES/$2.5\ \log_{10}$) treatment with Factor H. mRNA expression of IL-12 was found to be enhanced in ($1\ \log_{10}$) subtype at 6 h following factor H treatment, but increased levels were seen in H3N2 infected cells at both 2 h and 6 h treatment (FIG. 7B).

Figure 8A:
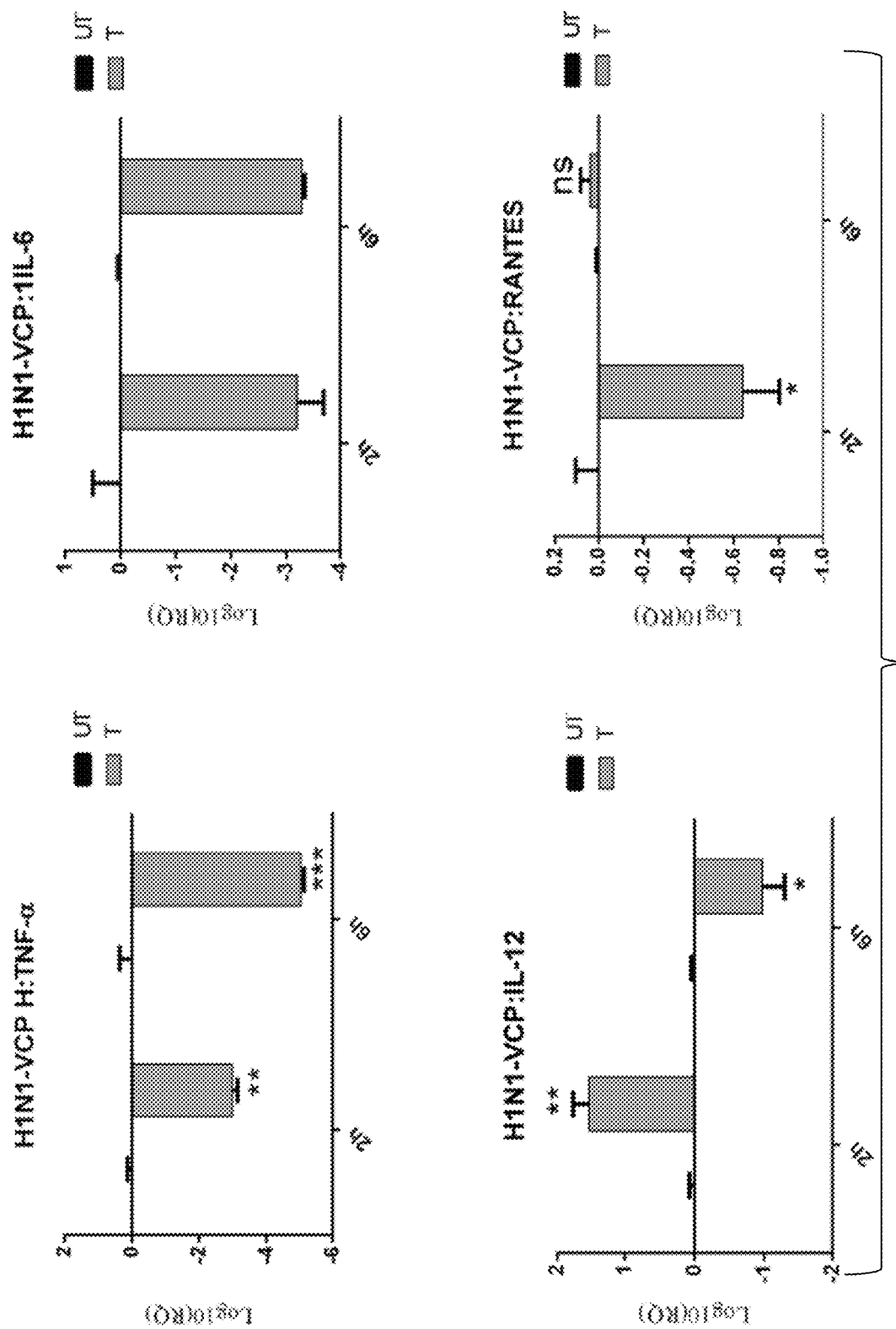
Figure 8B:
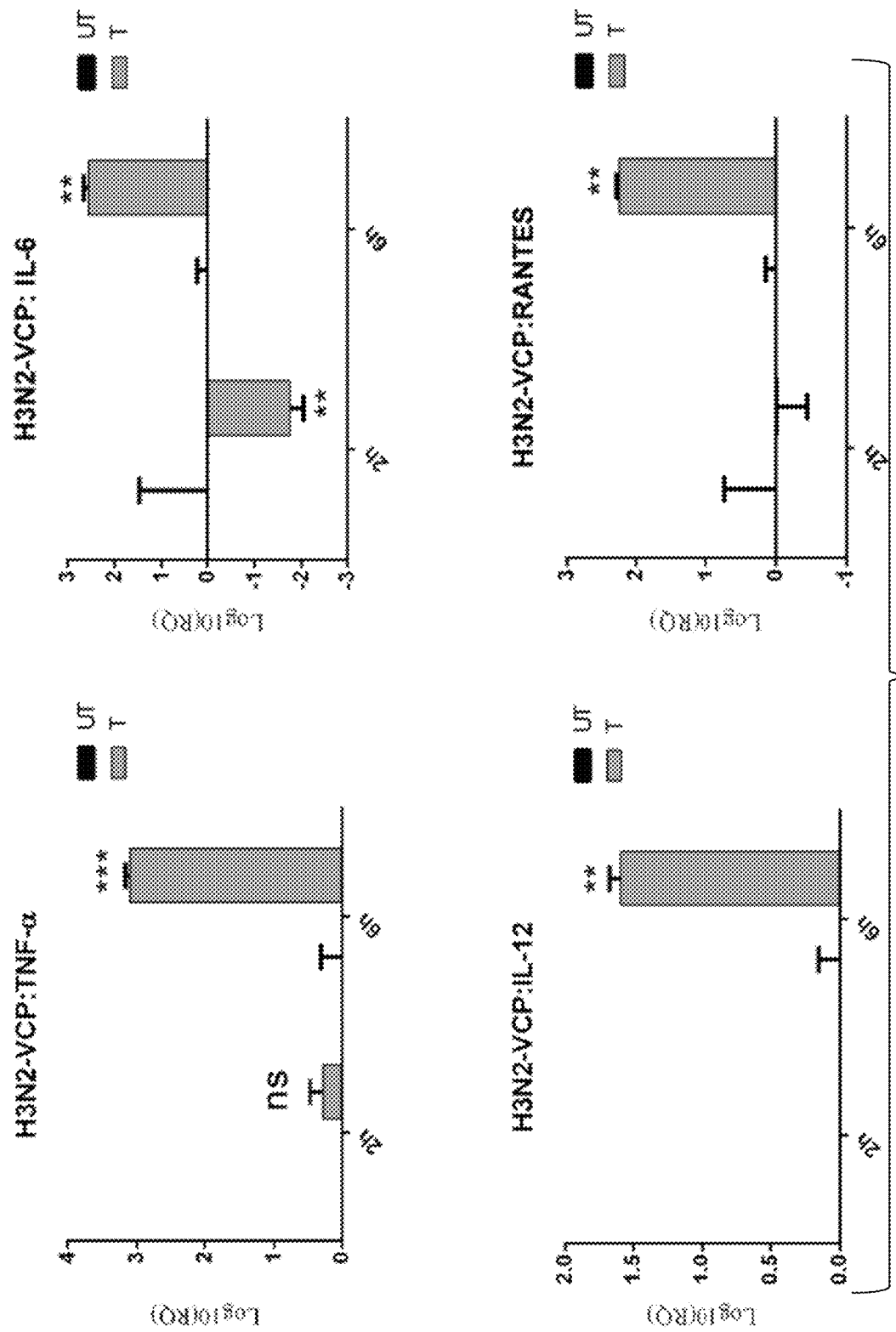

In the case of VCP treatment, TNF-α ($-5\ \log_{10}$) IL-6 ($-3.5\ \log_{10}$), IL-12 ($-1.5\ \log_{10}$) levels were found to be down-regulated at 6 h treatment when compared to untreated control (cells+H1N1) (FIGS. 8A and 8B). H1N1 infected cells treated with VCP shows reduced levels of RANTES ($-0.7\ \log_{10}$) at 2 h. However, H3N2 infected cells following VCP treatment has revealed similar effects as factor H. Briefly, upregulation of TNF-α, IL-6, IL-12, and RANTES were observed at 6 h VCP treatment (FIG. 8A). This corresponds to previous studies as enhanced levels of pro-inflammatory cytokines, including TNF-α, IL-6 and IFN-α were detected in individuals infected with IAV (Duvigneau et al., 2016). IL-6, and TNF-α may be the key contributors in virus mediated respiratory diseases, including Acute Respiratory Distress syndrome (ARDS) or acute lung injury (Cheng et al. 2011). During influenza infection, alveolar macrophages are activated, which are the primary phagocytic cells that produce robust amounts of IL-6 and TNF-α. Macrophages infected with Influenza have also shown to produce chemokines such as RANTES and monocytes chemotactic protein-1 (MCP-1). This further recruits mononuclear cells to the lungs and facilitate viral clearance (Kaufmann et al. 2001) and enhances production of those cytokines that are also implicated in the pathogenesis of influenza virus. RANTES, IL-1β, IL-6 and TNF-α induced by influenza resulted in pro-inflammatory Th1-type immune response in the infected host. Dysregulation of cytokines and chemokines levels during influenza has been demonstrated to promote tissue injury and impaired viral clearance. Additionally, suppression of IFN-α was also evident with factor H and VCP treatment at 6 h (FIG. 8C) in H1N1 infected cells. In the case of H3N2, both factor H and VCP increased the expression of IFN-α. Downregulation of IFN-α levels in H1N1 infected cells shows that factor H and VCP treatment can be used reduce the rate of viral replication. Thus, treatments with factor H and VCP elicit anti-viral response in A549 cells, restricting the activation of innate immune cells and associated lung pathology.

Figure 9A:
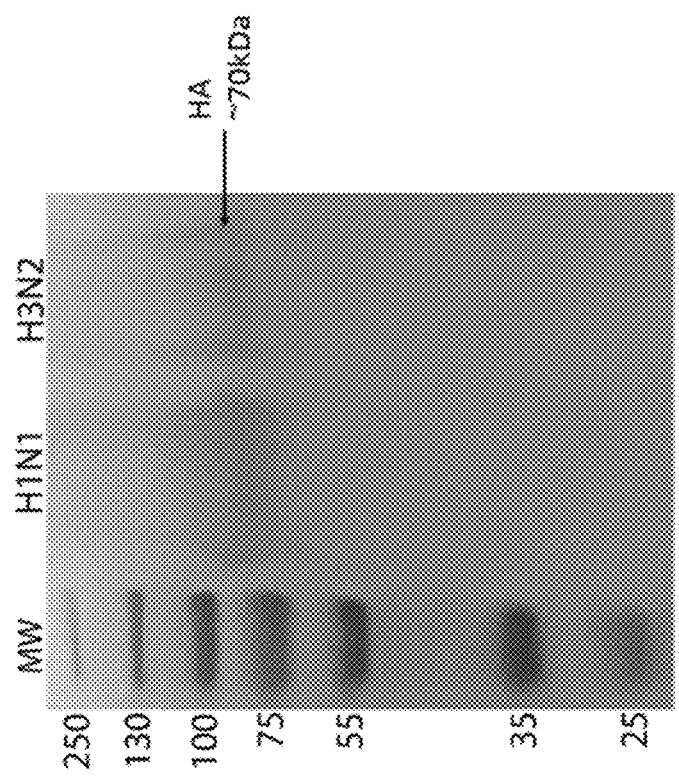
Figure 9B:
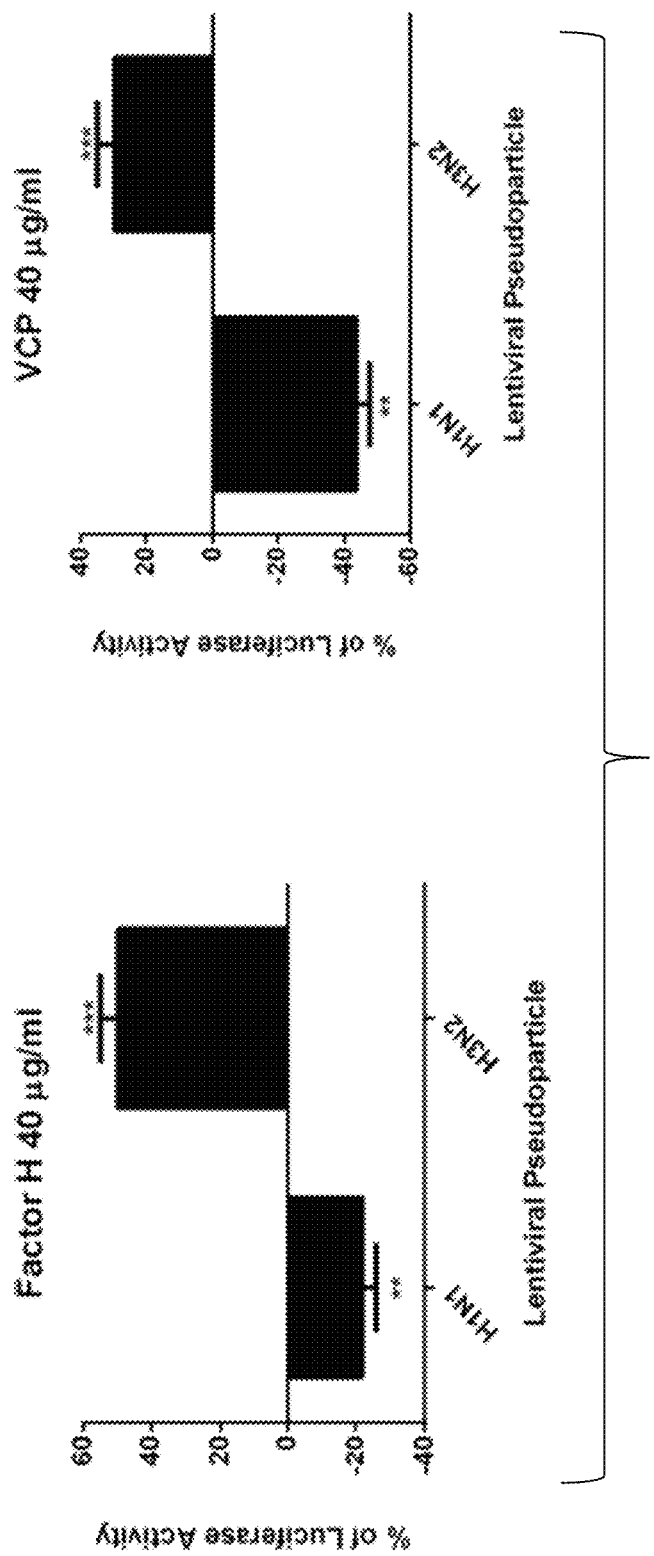

Targeting viral entry into a host cell is an emerging approach for developing anti-viral therapy as viral propagation can be either restricted or blocked at an early stage of viral cycle, minimizing drug resistance by released virions. In this study, we have generated lentiviral pseudotypes, a safe surrogate model to mimic the structure and surfaces of IAV, and to determine where factor H and VCP act as an entry inhibitor in cells transduced with pseudotyped IAV particles (H1N1 and H3N2) that are restricted to only one replicative cycle. The lentiviral particles pseudotyped with H1N1 and H3N2 were assessed via western blotting using anti-HA polyclonal antibody (FIG. 9A). 40 µg/ml of factor H treatment resulted in 25% reduction of luciferase reporter activity in MDCK cells transduced with H1N1 pseudotyped particles (FIG. 9B). However, addition of factor H increased the luciferase activity by 50% in cells challenged with H3N2 pseudotyped particles. VCP was found to reduce luciferase reporter activity of H1N1 transduced MDCK cells by 45% with 40 µg/ml VCP (FIG. 9B). However, similarly to factor H, VCP also enhanced the reporter activity of MDCK cells transduced with H3N2 pseudotyped lentiviral particles by 30%.

In conclusion, restricting of M1 mRNA levels, pro-inflammatory cytokine response, and luciferase reporter activity suggests and heights the ability of both factor H and VCP to act as an entry inhibitor against H1N1 subtype, and their action is strain specific.

Examples

1. Materials and Methods
Materials and Methods
Viruses and Reagents

The IAV subtypes used in this study, including the pH1N1 (A/England/2009), and H3N2 (A/HK/1999) was provided by Wendy Barclay (Imperial College, London), and Leo Poon (University of Hong Kong). The plasmids used for the production of H1N1 and H3N2 pseudo-typed viral particles were obtained from Addgene; pHIV-Luciferase (Addgene plasmid #21375); psPAX2 (Addgene plasmid #12260); and Vesicular Stomatitis Virus (VSV-G) (Addgene plasmid #8454). pcDNA3.1-swineH1-flag (H1 from swine H1N1 A/California/04/09) (Invitrogen), pcDNA3.1-swine N1-flag (N1 from swine H1N1 A/California/04/09), and pCDNA H3 (from A/Denmark/70/03 (H3N2) (Invitrogen). pI.18-N2 [N2 from A/Texas/50/2012/(H3N2)] plasmid was a gift from Nigel Temperton (University of Kent). Anti-influenza antibodies used were obtained from BEI Resources, NIAID, NIH, USA, and used as previously described (Al-Ahdal et al. 2018); including polyclonal anti-influenza Virus H3 HA, A/Hong Kong/1/1968 and monoclonal anti-influenza virus H1 HA, A/California/04/2009.

Purification of Human Complement Factor H

Complement factor H was purified, as described by Sim et al. (Sim et al. 1993) from human plasma, using an antibody column that has a monoclonal antibody against human factor H (MRCOX23) coupled to CNBr-activated Sepharose (GE healthcare, UK). Freshly thawed human plasma (Fisher-Scientific) was made 5 mM EDTA, pH 8 and dialysed overnight against Buffer I (25 mM Tris-HCL, 140 mM NaCl, and 0.5 mM EDTA, pH 7.5). The MRCOX23 Sepharose column was washed with three column bed volumes of buffer I, and dialysed plasma was passed. The column was then re-washed again with the same buffer and factor H was eluted using 3M $MgCl_2$ at pH 6.8. The eluted fractions were then dialysed against $H_2O$ overnight, followed by 10 mM potassium phosphate pH 7.4. The samples were then analysed for purity by 12% SDS-PAGE.

Purification of Vaccinia Virus Complement Control Protein in HEK293 Cell Line

The Vaccinia virus complement control protein (VCP) (accession XI3166.1) was codon-optimized for human expression by GeneArt® using GeneOptimizer® technology (Geneart GmbH, Regensburg). For lentiviral expression, amplified VCP cDNA was ligated into the pLenti6/V5-D-TOPO vector, using the ViraPower Lentiviral Directional TOPO Expression kit according to manufacturer's instructions (K4950-00 Invitrogen Corp, Carlsbad Calif.). Following transformation into DH5-alpha chemically competent E. coli cells, a number of colonies were analyzed for correct insertion and orientation using colony PCR. Transient transfection of the plasmid pLenti6/V5/VCP in HeLa cells and indirect immunofluorescence using anti-V5 antibody (Invitrogen #R960-25) was performed to verify the VCP expression. Replication-incompetent lentiviral stock was made by co-transfection with the ViraPower™ Packaging Mix (pLP1, pLP2, and pLP/VSVG: K4975-00, Invitrogen Corp) in human 293FT (human embryonic kidney, ATCC CRL-1573) cells using Lipofectamine 2000® reagent (Life Technologies Inc), according to the manufacturer's instructions. 48 h after co-transfection, viral supernatant was collected, concentrated by centrifugation, and the titer was determined using standard procedures. A number of stable 293FT cell lines expressing VCP were generated under neomycin selection (0.5 g/L) and screened for VCP expression by Western blot analysis. Three clones of HEK-293 cells carrying the VCP gene and secreting high levels of the VCP were selected and cultured. Secreted VCP was purified through a heparin column. Column-bound proteins were eluted with a linear salt gradient (0 to 0.5 M NaCl). Fractions were collected and analyzed via SDS-PAGE and western blotting.

Cell Culture and Treatments

The cell lines used in this study, including the Madin Darby Canine Kidney (MDCK), Adenocarcinomic human alveolar basal epithelial cells (A549), and human embryonic kidney (HEK) 293T cells (ATCC, Rockville, Md., USA) were cultured in complete DMEM media, supplemented with 10% v/v fetal calf serum, 2 mM 1-glutamine, and penicillin (100 U/ml)/streptomycin (100 µg/ml) (Thermo Fisher). Cells were grown at 37° C. under 5% v/v $CO_2$, with fresh complete medium every 2-3 days until 80% confluence was reached. All the cell lines used in this study were subjected to less than seven passages for all the in vitro experiments.

Production of IAV Subtypes, Pseudotyped Viral Particles, and TCID50 (Median Tissue Culture Infectious Dose) Assay 50,000 MDCK cells at 80% confluency were infected either with pH1N1 ($2\times10^4$) or H3N2 ($3.3\times10^4$) particles, and incubated in complete DMEM medium at 37° C. for 1 h. Unbound viral particles were removed, and replaced with infection medium, composed of DMEM with 0.3% bovine serum albumin (BSA), 1% penicillin/streptomycin, and 1 µg/ml of 1-1-Tosylamido-2-phenylethyl chloromethyl ketone (TPCK)-Trypsin (Sigma-Aldrich), and incubated for 3 days under culture conditions as mentioned above. Post infection, supernatant was subjected to ultra-centrifugation (25,000×g) for 90 minutes at 4° C. Purified viral particles were then re-suspended in PBS, and purity of the virus was analysed by SDS-PAGE and western blotting. Production of pseudotyped particles was carried out as published earlier (Al-Adhal et al. 2018). Briefly, HEK293T cells were co-transfected with 20 µg of respective IAV pCDNAs; including pcDNA3.1-swineH1-flag (H1 from swine H1N1 A/California/04/09) (Invitrogen), pcDNA3.1-swine N1-flag (N1 from swine H1N1 A/California/04/09) (Invitrogen), pcDNA-H3 [H3 from A/Denmark/70/03/(H3N2)], pI.18-N2 [N2 from A/Texas/50/2012/(H3N2)], pHIV-Luciferase backbone (Addgene), and psPAX2 (Addgene). VSV-G was generated similarly as described above, without H1N1 and H3N2 pcDNAs. The released H1N1, H3N2 and VSY-G pseudotyped lentiviral particles were harvested in the form of supernatant at 48 h. Harvested supernatant was centrifuged at 5,000×g for 20 minutes, and the clear supernatant without any debris was concentrated using ultra centrifugation (25,000×g) for 90 mins. The ultra-centrifuged lentiviral particles were re-suspended in sterile PBS, and were analysed via TCID50, western blotting and luciferase activity assay. TCID50 assay was carried out to determine the viral titre, and cytopathic effects (CPE) of infected cells (Hollý et al. 2017). Briefly, MDCK cells ($1 \times 10^3$) were transfected with either purified pH1N1 and H3N2 viral parties or pseudotyped lentiviral particles, incubated at 37° C. for 3 days under 5% v/v $CO_2$ until cytopathic effect (CPE) was observed in terms of structural changes in MDCK cells that were caused by viral invasion.

Hemagglutination Inhibition Assay

In 96 microtiter well plate, 25 µl of 1×PBS was added to each well. In the first column, starting concentration (total volume 50 µl) of 20 µg of fH, were serially diluted (25 µl) to achieve final quantities of 20, 10, 5, and 2.5 µg of fH per well. Controls used were no protein and PBS only. 25 µl of respective IAV subtype particles were added to wells except for PBS control wells at dilutions corresponding to their respective HA titre to initiate hemagglutination. Plate was gently mixed and incubated at 37° C. for 1 h. 50 µl of 0.75% guinea pig RBCs (V:V in PBS) was added to each well, plates were gently mixed, and incubated at room temperature for 1 h. Inhibition of hemagglutination appeared as halo or circle of settled cells in the centre of round-bottomed plates. Absence of inhibition was evident from a uniform reddish colour across the well (hemagglutination).

Direct ELISA to Detect Interaction of Factor H and VCP with IAV Subtypes

Factor H or VCP [5, 2.5, 1.25, and 0.625 µg/well (100 µl/well)] were coated onto 96-well plates using carbonate-bicarbonate buffer (CBC), pH 9.6, and incubated at 4° C. overnight. After washing the microtiter wells with PBS, the protein coated wells were blocked with 2% w/v BSA in PBS, and incubated at 37° C. for 2 h, followed by three PBST (PBS+0.05% Tween 20) washes. 20 µl of H1N1 or H3N2 virus ($1.36 \times 10^6$ pfu/ml) in PBS were added to each well, and incubated at 37° C. for 2 h in the presence of 5 mM $CaCl_2$. VSV-G pseudotyped lentivirus was used as a negative control. Following PBST washes, the corresponding wells were incubated with primary antibodies (100 µl/well); polyclonal anti-influenza virus H3 and monoclonal anti-influenza virus H1 (1:5000) (BEI-Resources). The wells were again washed with PBST three times, and probed with Protein A-HRP-conjugate, or anti-mouse IgG-Horseradish peroxidase (HRP)-conjugate (1:5000) (Fisher Scientific), followed by incubation at 37° C. for 1 h. Colour was developed using 3,3', 5,5'-Tetramethylbenzidine (TMB) substrate (Sigma-Aldrich), and reaction was stopped using 1M $H_2SO_4$, followed by measuring absorbance at 450 nm using iMark™ microplate absorbance reader (Bio-Rad).

Cell Binding Assay to Detect IAV Interference with Factor H and VCP

Cultured A549 cells ($1 \times 10^5$ cells/well) were seeded in 96 microtiter wells, and incubated at 37° C. overnight in 5% v/v $CO_2$. Once the desired cell confluency (80%) was reached, the cells were washed twice with sterile PBS. A varied concentration of fH or VCP (10, 5, 2.5, 1.25 µg/ml) pre-incubated with H1N1 and H3N2 ($1.36 \times 10^6$ pfu/ml) IAV subtypes were added to the wells, in addition to 5 mM $CaCl_2$, and incubated at room temperature for 2 h. BSA was added in the similar way, and used as a negative control. Following washes with PBS three times, the corresponding wells were fixed with 4% paraformaldehyde (Fisher Scientific) for 5 min at room temperature. The wells were then blocked with 2% BSA diluted in PBS for 2 h at 37° C. Polyclonal anti-influenza virus H3 (BEI-Resources), and monoclonal anti-influenza H1 (BEI-Resources) was added to the corresponding wells, and incubated at 37° C. for 1 h. After gentle washes with PBS-tween 20 (0.05%), the wells were probed with protein A-HRP conjugate, and goat anti-mouse IgG-HRP-conjugate (Thermo-Fisher) diluted in PBS in 1:5000 dilution, and incubated at 37° C. for 1 h. The wells were introduced to another wash with PBS-tween 20 (0.05%), the colour was developed by adding TMB substrate; and the reaction was stopped by using 1M $H_2SO_4$. The absorbance was read at 450 nm using an ELISA plate reader.

Far-Western Blotting

As similarly described by Al-Ahdal et al. 2018, purified H1N1/H3N2 ($1.36 \times 10^6$ pfu/ml) virus was run on a 12% (w/v) SDS-PAGE, and transferred onto a PVDF membrane for 2 h at 320 mA in transfer buffer, containing 25 mM TrisHCl pH 7.5, 20% methanol, and 190 mM glycine. Membrane was blocked with PBS+5% w/v BSA (Sigma-Aldrich) at room temperature, followed by PBST washes. The membrane was then incubated with 10 µg/ml of fH or VCP overnight at 4° C., and probed with primary antibody; monoclonal mouse anti-human factor H (MRCOX23) (MRC Immunochemistry Unit, Oxford) (1 mg/ml) or polyclonal rabbit anti-VCP antibody (0.5 mg/ml) (King Faisal Specialist Hospital and Research Centre, Saudi Arabia) at room temperature for 1 h. Following PBST washes, three times 10 minutes each, the membrane was incubated with secondary antibody, rabbit anti-mouse IgG HRP conjugate (1:1,000) (Sigma-Aldrich) or Protein A-HRP-conjugate for 1 h at room temperature. The secondary antibody was removed, followed by PBST washes, the membrane was developed using 3,3'-diaminobenzidine (DAB).

Infection Assay for Extracting RNA

A549 ($5 \times 10^5$/well) cells were cultured in complete DMEM, and grown overnight at 37° C. in $CO_2$ incubator. Once 85% cell confluency was reached, the cells were washed gently with fresh PBS, and replaced with pure DMEM without FBS. 40 µg/ml of fH or VCP was added to corresponding wells, with MOI 1 of pH1N1, and H3N2 or pseudotyped viral particles (333 µl/ml) at room temperature for 1 h and at 4° C. for another 1 h. The unbound virus and protein were removed by pipetting out the supernatant, and the cells were washed gently again with PBS, and placed in 1 ml of infection medium to initiate viral infection in host cells, and incubated for 2 and 6 h. After removing the supernatant, the infected cells were washed with PBS, and detached using 2× Trypsin-EDTA (0.5%) (Fisher Scientific), followed by centrifugation at 1500×g for 5 mins, and the cell pellet was frozen at −80° C. for RNA extraction.

Quantitative RT-PCR Analysis

The virus infected cell pellets were lysed using lysis buffer, containing 50 mM Tris-HCl pH 7.5, 200 mM NaCl, 5 mM EDTA pH 8, 0.1% v/v Triton X-100. GenElute Mammalian Total RNA Purification Kit (Sigma-Aldrich) was used to extract the total RNA as per manufacturer's instructions. Once RNA was extracted, DNase I (Sigma-Aldrich) treatment was performed to remove any DNA contaminants, followed by quantifying the amount of RNA at A260 nm using a NanoDrop 2000/2000c (Fisher-Scientific). The purity of RNA was assessed using the ratio A260/A280. 2 µg of total RNA was used to synthesise cDNA, using High Capacity RNA to cDNA Kit (Applied Biosystems) and cDNA conversion was performed as per protocol. The primer BLAST software (Basic Local Alignment Search Tool) was used to design primer sequences as listed in table 1. The qRT-PCR assay was performed using the Light Cycle System (Applied Biosciences). Each qPCR reaction was conducted in triplicates, containing 75 nM of forward and reverse primers, 5 µl Power SYBR Green MasterMix (Applied Biosystems), and 500 ng of cDNA. qPCR samples were run for 50° C. and 95° C. for 2 and 10 min, followed by running the amplification template for 40 cycles, each cycle involving 15 s at 95° C. and 1 min at 60° C. 18 s RNA was used as an endogenous control to normalise the gene expression.

Statistical Analysis

The graphs shown in this study were generated using the GraphPad Prism 6.0 software, and one-way ANOVA test was carried out as a statistical measure. Significant values were considered based on $*p<0.1$, $p<0.05$, $*p<0.01$, and 0.001 between protein treated and untreated conditions. Error bars show the SD or SEM, as indicated in the figure legends.

2. Results 2.1 Factor H Inhibits Hemagglutination of IAV Subtypes on Guinea Pig Red Blood Cells Factor H was purified from human plasma, using monoclonal MRCOX23 Sepharose affinity column. Purity of the $MgCl_2$ fractions was established by SDS-PAGE; the molecular weight of factor H was evident at ~155 kDa (FIG. 1) (Sim et al. 1993).

Hemagglutination assay was performed using guinea pig red blood cells to determine if addition of factor H would inhibit hemagglutination of IAV subtypes (FIG. 2). The basic principle of this assay relies on the specific feature of enveloped viral glycoproteins that can interact with sialic acid receptors on red blood cells (RBCs). In the absence of viral particles, RBCs is shown to precipitate by gravity to the bottom of microtiter plate, rising in a distinct red coloured halo at the bottom of the well. However, in the presence of viral particles, glycoproteins of virus (HA or NA in this case) interact and bind with sialic acid on RBCs, forming clumps and lead to a lattice formation. In order to establish the viral litre, IAV strains such as H3N2 (HK99, UD72) and H1N1 (WSN33, HK98, england09) were tested for hemagglutination to ascertain the HA titre of each IAV subtypes. Factor H partially inhibited the hemagglutination of IAV strains. It is possible that factor H binds to the IAV particles, restricting the binding of virus to RBCs, allowing them to form a halo at the bottom of the wells. Factor H (10 µg/ml) concentration was more effective against the H1N1 strains when compared to H3N2 IAV subtype. PBS alone in the absence of IAV particles led to formation of halo at the bottom of the microtiter well.

2.2 Factor H Binds IAV Envelope Glycoproteins

Since factor H was able to inhibit hemagglutination of IAV subtypes, direct ELISA was set up to establish possible interaction of factor H with IAV subtypes (FIG. 3). A greater dose dependent binding by factor H and VCP was evident with H1N1 subtype when compared to H3N2 (FIG. 3). VSV-G pseudotyped lentivirus was used as a negative control, which did not show any binding with factor H or VCP. The ability of factor H and VCP to bind to A549 cells, challenged with IAV subtypes, were assessed via cell binding assay (FIG. 4). Maximum cell binding was seen at a higher concentration (10 µg/ml) for both H1N1 and H3N2 IAV subtypes, and the binding occurred in a dose and calcium dependent manner (FIG. 4). These binding data appear to suggest that direct interaction of factor H and VCP with both HA and NA is likely to either interfere with viral infection of the target cells without involving complement activation. Factor H's ability to bind both HA and NA, and its weak binding with H3N2 is partially seems to be consistent with hemagglutination assay, where factor H may act as a potent inhibitor for H1N1 subtype compared to H3N2. In addition, a far western blotting technique was carried out to further validate the interaction of factor H and VCP with HA and NA, and to identify the interaction of additional viral proteins that may be binding to factor H and VCP (FIG. 5). In this assay, nitrocellulose membrane transferred viral subtypes (H1N1 and H3N2) were incubated with 10 µg/ml factor H and the blot was probed with anti-factor H antibodies, as well as anti-IAV antibodies. Far western blotting analysis confirmed the binding of factor H and VCP to HA (~70 kDa), and M1 (~25 kDa) of both H1N1 and H3N2 IAV subtypes (FIG. 5). However, factor H also bound to NA (~55 kDa) of H3N2 strain strongly when compared to H1N1 strain.

2.3 Modulation of IAV Infectivity by Factor H and VCP in Infected A549 Cells

In order to proof the binding of factor H to HA, NA, and M1 viral proteins modulates viral replication and infectivity, an infection assay was carried out to determine the mechanism of direct viral modulation on replication stage by factor H and VCP. Lung epithelial cells, A549 infected with H1N1 and H3N2 or pre-treated with factor H and VCP (40 µg/ml) showed differential expression of M1 at mRNA levels at both 2 h and 6 h treatment (FIG. 6). In the case of H1N1, both factor H and VCP showed down-regulation (−4 $\log_{10}$) of viral M1 expression at mRNA level at 6 h treatment. However, an up-regulation was seen with H3N2 (2 $\log_{10}$) subtype following factor H and VCP treatment, suggesting that the effect by these proteins is strain-specific (FIG. 6).

2.4 Factor H and VCP Trigger Anti-Inflammatory Response in the Case of H1N1, while Pro-Inflammatory Effect in H3N2 IAV Subtype Our qPCR data revealed that factor H and VCP treatment resulted in the modulation of both pro and anti-inflammatory response (FIGS. 7 and 8).

Following factor H treatment, the mRNA levels of TNF-α were downregulated at 2 h (−5 $\log_{10}$) and 6 h (−8 $\log_{10}$) in H1N1 infected cells (FIG. 7A). However, an opposite effect was seen with H3N2 infected cells; the expression levels of TNF-α was up-regulated at 2 h (3 $\log_{10}$) as well as at 6 h (3.5 $\log_{10}$) treatment (FIG. 7B). The mRNA levels of IL-6 (−3.5 $\log_{10}$) and RANTES (−0.5 $\log_{10}$) were downregulated at 2 h treatment with Factor H, which were brought up slightly at 6 h treatment. Conversely, IL-6 (2.5 $\log_{10}$) and RANTES (1.5 $\log_{10}$) levels were upregulated in H3N2 infected cells following 2 h and 6 h (IL-6/3 $\log_{10}$) (RANTES/(2.5 $\log_{10}$) treatment with Factor H. Factor H also down-regulated IL-12 levels in H1N1 (1 $\log_{10}$) subtype at 6 h, while enhanced in H3N2 infected cells at both 2 h and 6 h treatment.

Figure 8C:
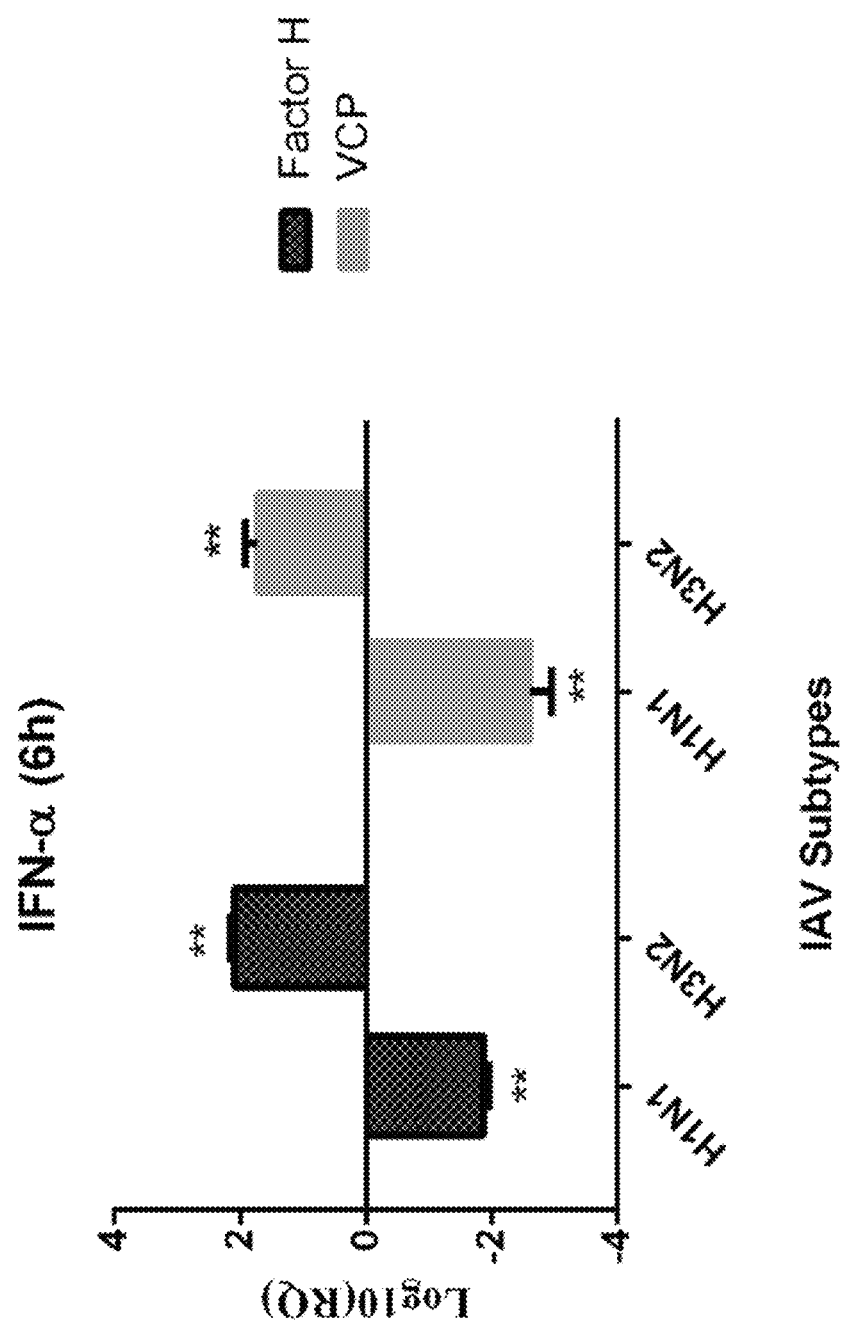

The effect of VCP, which contains CCP modules like human Factor H, mirrored the results obtained by Factor H (FIG. 8). A higher down-regulation of TNF-α (−5 $\log_{10}$) IL-6 (−3.5 $\log_{10}$), IL-12 (−1.5 $\log_{10}$) levels were seen at 6 h following VCP treatment when compared to untreated control (cells+H1N1) (FIG. 8A). VCP treated H1N1 infected cells showed a reduced level of RANTES at 2 h (−0.7 $\log_{10}$), which was brought up slightly at 6 h. In the case of H3N2, effects similar to factor H were observed with VCP treatment (FIG. 8B). TNF-α, IL-6, IL-12, and RANTES were increased at 6 h VCP treatment. Higher levels of pro-inflammatory cytokines, including TNF-α, IL-6 and IFN-α have been detected in IAV infected patients in previous experiments of others, and correlate with severe infectivity. H1N1 infected patients were seen with an enhanced levels of IL-6 in their lungs and serum (Kaiser et al. 2001; Hagau et al. 2010). Therefore, downregulation of IL-6 by both factor H and VCP on H1N1 infected A549 cells suggest the possible anti-inflammatory role of these proteins in a strain specific manner. In addition, ability of factor H (−2 $\log_{10}$) and VCP (2.5 $\log_{10}$) to downregulate type 1 IFN-α (FIG. 8C) at 6 h was also seen in H1N1. However, higher expression level of IFN-α was detected in the case of H3N2 strain (FIG. 8C); factor H (2 $\log_{10}$), and VCP (1.7 $\log_{10}$).

MDCK cells were transduced with purified H1N1 and H3N2 pseudotyped particles to measure the luciferase reporter activity with and without factor H and VCP (40 μg/ml) treatments. Nearly 25% reduction in the luciferase reporter activity was observed with 40 μg/ml of factor H compared to cells only challenged with H1N1 pseudotyped particles (FIG. 9B). However, factor H enhanced the luciferase activity by 50% in cells transduced with H3N2 pseudotyped particles. In the case of VCP treatments, addition of 40 μg/ml of VCP resulted in 45% reduction of luciferase activity, whereas VCP resulted in 30% increased luciferase activity in cells transduced with H3N2 pseudotyped particles (FIG. 9B).

These data show an entry inhibitory role of factor H and VCP against IAV is strain specific, factor H and VCP seem to act as an entry inhibitor only in the case of H1N1.

REFERENCES

Abdul-Aziz M, Tsolaki A G, Kouser L, Carroll M V, Al-Ahdal M N, Sim R B, Kishore U. Complement factor H interferes with *Mycobacterium bovis* BCG entry into macrophages and modulates the pro-inflammatory cytokine response. Immunobiology. 2016 September; 221(9): 944-52. doi: 10.1016/j.imbio.2016.05.011. Epub 2016 May 24.

TABLE 1

Target genes, forward and reverse primers used for qPCR

| Target | Forward Primer [SEQ ID NO.] | Reverse Primer [SEQ ID NO.] |
|---|---|---|
| 18S | 5'-ATGGCCGTTCTTAGTTGGTG-3' [SEQ ID NO. 1] | 5'-CGCTGAGCCAGTCAGTGTAG-3' [SEQ ID NO. 2] |
| IL-6 | 5'-GAAAGCAGCAAAGAGGCACT-3' [SEQ ID NO. 3] | 5'-TTTCACCAGGCAAGTCTCCT-3' [SEQ ID NO. 4] |
| IL-12 | 5'-AACTTGCAGCTGAAGCCATT-3' [SEQ ID NO. 5] | 5'-GACCTGAACGCAGAATGTCA-3' [SEQ ID NO. 6] |
| TNF-α | 5'-AGCCCATGTTGTAGCAAACC-3' [SEQ ID NO. 7] | 5'-TGAGGTACAGGCCCTCTGAT-3' [SEQ ID NO. 8] |
| M1 | 5'-AAACATATGTCTGATAACGAAGGAGA ACAGTTCTT-3' [SEQ ID NO. 9] | 5'GCTGAATTCTACCTCATGGTCTTC TTGA-3' [SEQ ID NO. 10] |
| RANTES | 5'-GCGGGTACCATGAAGATCTCTG-3' [SEQ ID NO. 11] | 5'-GGGTCAGAATCAAGAAACCCTC-3' [SEQ ID NO. 12] |
| IFN-α | 5'-TTT CTC CTG CCT GAA GGA CAG-3' [SEQ ID NO. 13] | 5'-GCT CAT GAT TTC TGC TCT GAC A-3' [SEQ ID NO. 14] |

2.4 Factor H and VCP as an Entry Inhibitor of H1N1 Subtype of IAV

In this study, lentiviral pseudotypes were generated as a highly versatile and useful system to determine cell entry strategies of H1N1 and H3N2 subtype of IAV. Production of lentiviral pseudotypes were carried out by co-transfecting HEK293T cells with plasmid containing the coding sequence of IAV glycoproteins variants such as H1+N1, and H3+N2, pHIV-Luciferase backbone, and psPAX2 plasmids via calcium phosphate transfection method. Post transfection, purified H1N1 and H3N2 pseudotypes particles were harvested at 48 h, and analysed via western blotting and the HA expression level was detected using anti-H1 polyclonal antibody; HA was evident around ~70 kDa (FIG. 9A).

Ansari M, McKeigue P M, Skerka C, Hayward C, Rudan 1, Vitart V, Polasek O, Armbrecht A M, Yates J R, Vatavuk Z, Bencic G, Kolcic I, Oostra B A, Van Duijn C M, Campbell S, Stanton C M, Huffman J, Shu X, Khan J C, Shahid H, Harding S P, Bishop P N, Deary I J, Moore A T, Dhillon B, Rudan P, Zipfel P F, Sim R B, Hastie N D, Campbell H, Wright A F. Genetic influences on plasma CFH and CFHR1 concentrations and their role in susceptibility to age-related macular degeneration. Hum Mol Genet. 2013 Dec. 1; 22(23):4857-69. doi: 10.1093/hmg/ddt336. Epub 2013 Jul. 19

Cheng X W, Lu J, Wu C L, Yi L N, Xie X, Shi X D, Fang S S, Zan F I, Kung H F, He M L. Three fatal cases of pandemic 2009 influenza A virus infection in Shenzhen are associated with cytokine storm. Respir Physiol Neurobiol. 2011 Jan. 31; 175(1): 185-7. doi: 10.1016/j.resp.2010.11.004.

Cox R J, Brokstad K A, Ogra P. Influenza virus: immunity and vaccination strategies. Comparison of the immune response to inactivated and live, attenuated influenza vaccines. Scand J Immunol. 2004 January; 59(1):1-15.

Duvigneau S, Sharma-Chawla N, Boianelli A, Stegemann-Koniszewski S, Nguyen V K, Bruder D, Hernandez-Vargas E A. Hierarchical effects of pro-inflammatory cytokines on the post-influenza susceptibility to pneumococcal coinfection. Sci Rep. 2016 Nov. 22; 6:37045. doi: 10.1038/srep37045

Fouchier R A, Munster V, Wallensten A, Bestebroer T M, Herfst S, Smith D, Rimmelzwaan G F, Olsen B, Osterhaus A D. Characterization of a novel influenza A virus hemagglutinin subtype (H16) obtained from black-headed gulls. J Virol. 2005 March; 79(5):2814-22

Ganesh V K, Smith S A, Kotwal G J, Murthy K H. Structure of vaccinia complement protein in complex with heparin and potential implications for complement regulation. Proc Natl Acad Sci USA. 2004 Jun. 15; 101 (24):8924-9

Haapasalo K, van Kessel K, Nissila E, Metso J, Johansson T, Miettinen S, Varjosalo M, Kirveskari J, Kuusela P, Chroni A, Jauhiainen M. van Strijp J, Jokiranta T S. Complement Factor H Binds to Human Serum Apolipoprotein E and Mediates Complement Regulation on High Density Lipoprotein Particles. J Biol Chem. 2015 Nov. 27; 290(48):28977-87. doi: 10.1074/jbc.M115.669226. Epub 2015 Oct. 14.

Hagau N, Slavcovici A, Gonganau D N, Oltean S, Dirzu D S, Brezoszki E S, Maxim M, Ciuce C, Mlesnite M, Gavrus R L, Laslo C, Hagau R, Petrescu M, Studnicska D M. Clinical aspects and cytokine response in severe H1N1 influenza A virus infection. Crit Care. 2010; 14(6):R203. doi: 10.1186/cc9324. Epub 2010 Nov. 9.

Haupt K, Reuter M, van den Elsen J, Burman J, Hälbich S, Richter J. Skerka C, Zipfel P F. The *Staphylococcus aureus* protein Sbi acts as a complement inhibitor and forms a tripartite complex with host complement Factor H and C3b. PLoS Pathog. 2008 December; 4(12):e1000250. doi: 10.1371/journal.ppat.1000250. Epub 2008 Dec. 26.

Heinekamp T, Schmidt H, Lapp K, Pähtz V, Shopova I, Köster-Eiserfunke N, Kruger T, Kniemeyer O, Brakhage A A. Interference of *Aspergillus fumigatus* with the immune response. Semin Immunopathol. 2015 March; 37(2):141-52. doi: 10.1007/s00281-014-0465-1. Epub 2014 Nov. 18

Hellwage J, Meri T, Heikkilä T, Alitalo A, Panelius J, Lahdenne P, Seppälä I J, Meri S. The complement regulator factor H binds to the surface protein OspE of *Borrelia burgdorferi*. J Biol Chem. 2001 Mar. 16; 276 (11):8427-35. Epub 2000 Dec. 11.

Herold S, Becker C, Ridge K M, Budinger G R. Influenza virus-induced lung injury: pathogenesis and implications for treatment. Eur Respir J. 2015 May; 45(5):1463-78. doi: 10.1183/09031936.00186214. Epub 2015 Mar. 18

Hogan B L, Barkauskas C E, Chapman H A, Epstein J A, Jain R, Hsia C C, Niklason L, Calle E, Le A, Randell S H, Rock J, Snitow M, Krummel M, Stripp B R, Vu T, White E S, Whitsett J A, Morrisey E E. Repair and regeneration of the respiratory system: complexity, plasticity, and mechanisms of lung stem cell function. Cell Stem Cell. 2014 Aug. 7;15(2): 123-38. doi: 10.1016/j.stem.2014.07.012.

Isaacs S N, Kotwal G J, Moss B. Vaccinia virus complement-control protein prevents antibody-dependent complement-enhanced neutralization of infectivity and contributes to virulence. Proc Natl Acad Sci USA. 1992 Jan. 15; 89(2):628-32.

Janulczyk R, Iannelli F, Sjoholm A G, Pozzi G, Bjorck L. Hie, a novel surface protein of *Streptococcus pneumoniae* that interferes with complement function. J Biol Chem. 2000 Nov. 24; 275(47):37257-63.

Kaiser L, Fritz R S, Straus S E, Gubareva L, Hayden F G. Symptom pathogenesis during acute influenza: interleukin-6 and other cytokine responses. J Med Virol. 2001 July; 64(3):262-8

Kandasamy M, Ying P C, Flo A W, Sumatoh H R, Schlitzer A, Hughes T R, Kemeny D M, Morgan B P, Ginhoux F, Sivasankar B. Complement mediated signaling on pulmonary CD103(+) dendritic cells is critical for their migratory function in response to influenza infection. PLoS Pathog. 2013 January; 9(1):e1003115. doi: 10.1371/journal.ppat.1003115.

Kaufmann A, Salentin R, Meyer R G, Bussfeld D, Pauligk C, Fesq H, Hofmann P, Nain M, Gemsa D, Sprenger H. Defense against influenza A virus infection: essential role of the chemokine system. Immunobiology. 2001 December; 204(5):603-13.

Khatua B, Ghoshal A, Bhattacharya K, Mandal C, Saha B, Crocker P R, Mandal C. Sialic acids acquired by *Pseudomonas aeruginosa* are involved in reduced complement deposition and siglec mediated host-cell recognition. FEBS Lett. 2010 Feb. 5; 584(3):555-61. doi: 10.1016/j.febslet.2009.11.087. Epub 2009 Nov. 27

Kotwal G J, Isaacs S N, McKenzie R, Frank M M, Moss B. Inhibition of the complement cascade by the major secretory protein of vaccinia virus. Science. 1990 Nov. 9; 250(4982): 827-30

Kraiczy P, Hartmann K, Hellwage J, Skerka C, Kirschfink M, Brade V, Zipfel P F, Wallich R, Stevenson B. Immunological characterization of the complement regulator factor H-binding CRASP and Erp proteins of *Borrelia burgdorferi*. Int J Med Microbiol. 2004 April; 293 Suppl 37:152-7.

Lam W Y, Tang J W, Yeung A C, Chiu L C, Sung J J, Chan P K. Avian influenza virus A/HK/483/97(H5N1) NS1 protein induces apoptosis in human airway epithelial cells. J Virol. 2008 March; 82(6):2741-51. doi: 10.1128/JVI.01712-07.

Lambris J D, Ricklin D, Geisbrecht B V. Complement evasion by human pathogens. Nat Rev Microbiol. 2008 February; 6(2): 132-42. doi: 10.1038/nrmicro1824.

McAuley J L, Corcilius L, Tan H X, Payne R J, McGuckin M A, Brown L E. The cell surface mucin MUC1 limits the severity of influenza A virus infection. Mucosal Immunol. 2017 November; 10(6):1581-1593. doi: 10.1038/mi.2017.16. Epub 2017 Mar. 22

Medina R A, García-Sastre A. Influenza A viruses: new research developments. Nat Rev Microbiol. 2011 Jul. 11; 9(8):590-603. doi: 10.1038/nrmicro2613.

Meri S, Pangburn M K. Discrimination between activators and nonactivators of the alternative pathway of complement: regulation via a sialic acid/polyanion binding site on factor H. Proc Natl Acad Sci USA. 1990 May; 87(10): 3982-6

Meri T, Amdahl H, Lehtinen M J, Hyvärinen S, McDowell J V, Bhattacharjee A, Meri S, Marconi R, Goldman A, Jokiranta T S. Microbes bind complement inhibitor factor H via a common site. PLoS Pathog. 2013; 9(4):e1003308. doi: 10.1371/journal.ppat.1003308.

Pizza M, Donnelly J, Rappuoli R. Factor H-binding protein, a unique meningococcal vaccine antigen. Vaccine. 2008 Dec. 30; 26 Suppl 8:146-8 *Proc Natl Acad Sci USA*.

Qian W, Wei X, Guo K, Li Y, Lin X, Zou Z, Zhou H, Jin M. The C-Terminal Effector Domain of Non-Structural Protein 1 of Influenza A Virus Blocks IFN-β Production by Targeting TNF Receptor-Associated Factor 3. Front Immunol. 2017 Jul. 3; 8:779.

Rattan A, Kasbe R, Mullick J, Sahu A. The complement system as a viral target for immune evasion. In: Kishore U, Nayak A, eds. *Microbial Pathogenesis: Infection and Immunity*. Austin: Landes Bioscience and Springer, 2013: 1-27

Sahu A, Pangburn M K. Identification of multiple sites of interaction between heparin and the complement system. Mol Immunol. 1993 May; 30(7):679-84

Sim R B, Day A J, Moffatt B E, Fontaine M. Complement factor I and cofactors in control of complement system convertase enzymes. Methods Enzymol. 1993; 223:13-35.

Simon N, Lasonder E, Scheuermayer M, Kuehn A, Tews S, Fischer R, Zipfel P F, Skerka C, Pradel G. Malaria parasites co-opt human factor H to prevent complement-mediated lysis in the mosquito midgut. Cell Host Microbe. 2013 Jan. 16; 13(1):29-41. doi: 10.1016/j.chom.2012.11.013. Epub 2013 Jan. 16.

Tscherne D M, García-Sastre A. Virulence determinants of pandemic influenza viruses. J Clin Invest. 2011 January; 121 (1):6-13. doi: 10.1172/JCI44947.

Vogl G, Lesiak I, Jensen D B, Perkhofer S, Eck R, Speth C, Lass-Flörl C, Zipfel P F, Blom A M, Dierich M P, Würzner R. Immune evasion by acquisition of complement inhibitors: the mould *Aspergillus* binds both factor H and C4b binding protein. Mol Immunol. 2008 March; 45(5): 1485-93.

Webster R G, Bean W J, Gorman O T, Chambers T M, Kawaoka Y. Evolution and ecology of influenza A viruses. Microbiol Rev. 1992 March; 56(1): 152-79.

Yang J, Liu S, Du L, Jiang S. A new role of neuraminidase (NA) in the influenza virus life cycle: implication for developing NA inhibitors with novel mechanism of action. Rev Med Virol. 2016 July; 26(4):242-50. doi: 10.1002/rmv.1879.

---

The invention claimed is:

1. A method for inducing the entry and/or replication of influenza A virus (IAV) subtype H3N2 in a cell, wherein said method comprises contacting the cell with vaccinia virus complement control protein (VCP), factor H and/or a complement control protein (CCP)-containing protein.

2. The method of claim 1, wherein the CCP-containing protein is a C4b binding protein.

3. A method for inhibiting the entry and/or replication of IAV subtype H1N1 in a cell, wherein said method comprises contacting the cell with vaccinia virus complement control protein (VCP), factor H and/or a complement control protein (CCP)-containing protein.

4. The method of claim 3, wherein the method further comprises detecting the expression level of hemagglutinin (HA), neuraminidase (NA), and/or matrix protein 1 (M1) of IAV subtype H1N1.

5. The method of claim 3, wherein the inhibition is complement independent.

6. A method for inducing the entry and/or replication of a pathogen in a subject in need thereof, comprising the administration of a therapeutically amount of vaccinia virus complement control protein (VCP), factor H and/or contiguous complement control protein (CCP)-containing protein or a domain of VCP, factor H and/or CCP-containing protein, wherein said domain is a complement regulatory domain, wherein the pathogen is an influenza A virus (IAV) subtype H3N2.

7. The method of claim 6, wherein said domain is a CCP18-20 of factor H.

8. The method of claim 6, wherein the administration is intranasal, intratracheal and/or sublingual.

9. The method of claim 6, wherein the CCP-containing protein is a C4b binding protein.

10. A method for inhibiting the entry and/or replication of influenza A virus (IAV) subtype H1N1 in a subject in need thereof, comprising the administration of a therapeutically amount of vaccinia virus complement control protein (VCP), factor H and/or contiguous complement control protein (CCP)-containing protein or a domain of VCP, factor H and/or CCP-containing protein, wherein said domain is a complement regulatory domain, wherein the administration is intranasal, intratracheal and/or sublingual.

11. The method of claim 10, wherein the inhibition is complement independent.

* * * * *